United States Patent
Villa

(10) Patent No.: US 8,735,331 B2
(45) Date of Patent: May 27, 2014

(54) DISPLAY LIBRARY FOR ANTIBODY SELECTION

(75) Inventor: Alessandra Villa, Zürich (CH)

(73) Assignee: Philochem AG, Zurich (CH)

( * ) Notice: Subject to any disclaimer, the term of this patent is extended or adjusted under 35 U.S.C. 154(b) by 319 days.

(21) Appl. No.: 13/063,123

(22) PCT Filed: Sep. 7, 2009

(86) PCT No.: PCT/EP2009/006487
§ 371 (c)(1),
(2), (4) Date: Mar. 9, 2011

(87) PCT Pub. No.: WO2010/028791
PCT Pub. Date: Mar. 18, 2010

(65) Prior Publication Data
US 2011/0236372 A1    Sep. 29, 2011

Related U.S. Application Data

(60) Provisional application No. 61/095,901, filed on Sep. 10, 2008.

(51) Int. Cl.
*C40B 40/10* (2006.01)
(52) U.S. Cl.
USPC .............................................. 506/18
(58) Field of Classification Search
None
See application file for complete search history.

(56) References Cited

FOREIGN PATENT DOCUMENTS

WO    99/20749    4/1999

OTHER PUBLICATIONS

Azriel-Rosenfeld et al. (2003) Journal of Molecular Biology vol. 335 pp. 177 to 192.*
Yang et al. (1995) Journal of Molecular Biology vol. 254 pp. 392 to 403.*
Tomlinson, I.M., et al. "The repertoire of human germline VH sequences reveals about fifty groups of VH segments with different hypervariable loops." J Mol Biol. Oct. 5, 1992;227(3):776-98.
Tomlinson, I.M., et al. "The structural repertoire of the human V kappa domain." EMBO J. Sep. 15, 1995;14 (18):4628-38.
Iba, Y., et al. "Changes in the specificity of antibodies against steroid antigens by introduction of mutations into complementarity-determining regions of the V(H) domain." Protein Eng. May 1998;11(5):361-70.
Pini, A., et al. "Design and use of a phage display library. Human antibodies with subnanomolar affinity against a marker of angiogenesis eluted from a two-dimensional gel." J Biol Chem. Aug. 21, 1998;273(34):21769-76.
Giovannoni, L., et al. "Isolation of anti-angiogenesis antibodies from a large combinatorial repertoire by colony filter screening." Nucleic Acids Res. Mar. 1, 2000;29(5):E27.
Azriel-Rosenfeld, R., et al. "A human synthetic combinatorial library of arrayable single-chain antibodies based on shuffling in vivo formed CDRs into general framework regions." J Mol Biol. Jan. 2, 2004;335(1):177-92.
Volkel, T., et al. "Isolation of endothelial cell-specific human antibodies from a novel fully synthetic scFv library." Biochem Biophys Res Commun. Apr. 30, 2004;317(2):515-21.

(Continued)

*Primary Examiner* — Christian Boesen
(74) *Attorney, Agent, or Firm* — Dann, Dorfman, Herrell & Skillman; Kathleen D. Rigaut

(57) ABSTRACT

Synthetic antibody display library containing human germline antibody molecules with variation in VH CDR3 and VL CDR3 and at position 52 of VH CDR2, for screening and selection of antibody molecules specific for antigens of interest.

16 Claims, 6 Drawing Sheets

(56) References Cited

OTHER PUBLICATIONS

Kuhne, S.A., et al. "Isolation of recombinant antibodies against EspA and intimin of *Escherichia coli* 0157:H7." J Clin Microbiol. Jul. 2004;42(7):2966-76.

Silacci, M., et al. "Design, construction, and characterization of a large synthetic human antibody phage display library." Proteomics. Jun. 2005;5(9):2340-50.

Brack, S.S., et al. "Tumor-targeting properties of novel antibodies specific to the large isoform of tenascin-C." Clin Cancer Res. May 15, 2006;12(10):3200-8.

Silacci, M., et al. "Human monoclonal antibodies to domain C of tenascin-C selectively target solid tumors in vivo." Protein Eng Des Sel. Oct. 2006;19(10):471-8. Epub Aug. 22, 2006.

Benhar, I. "Design of synthetic antibody libraries." Expert Opin Biol Ther. May 2007;7(5):763-79.

Villa, A.M., et al. "Human antibody technology. Generation of phage display libraries and isolation of vascular targeting antibodies." ETH E-Collection, [Online]. Jan. 22, 2009:1-116. Retrieved from the Internet: <URL: e-collection.ethbib.ethz.ch/eserv/eth:31119/eth-31119-02.pdf> [retrieved on Feb. 1, 2010].

\* cited by examiner

A

B

C

D

DISPLAY LIBRARY FOR ANTIBODY SELECTION

The present application is §371 application of PCT/EP2009/006487 filed Sep. 7, 2009 which claims priority to U.S. Provisional Application No. 61/095,901 filed Sep. 10, 2008, the entire disclosure of each being incorporated by reference herein.

FIELD OF THE INVENTION

This invention relates to antibody display libraries and methods of using such libraries to select an antibody molecule with a desired antigen-binding property.

INTRODUCTION

Monoclonal antibodies are useful reagents for chemical, biological and pharmaceutical research, and are also increasingly used as therapeutic agents for the diagnosis of treatment of serious conditions. Indeed antibody-based pharmaceuticals represent the fastest growing class of pharmaceutical biotechnology with sales in 2006, which exceeded US $ 20 billion. Human monoclonal antibodies are particularly useful for pharmaceutical applications, compared with antibodies generated in rodents, which are immunogenic in humans.

The generation of human monoclonal antibodies has been revolutionized by the advent of human combinatorial antibody libraries in conjunction with powerful selection methodologies such as iterative colony filter screening [1, 2], phage display [3, 4] and ribosome display [5].

The ability to isolate binding specificities against a broad variety of antigenic determinants represents one of the most important pre-requisites for a library for most practical applications. Other desirable features include the ability to rapidly affinity mature antibody clones, if required for special applications, as well as the performance of individual antibody clones (expression yields, stability, solubility, oligomeric format, etc.).

The size of antibody libraries (i.e., the number of antibody clones) is an important factor contributing to the successful isolation of good quality binders against a variety of different antigens [6]. Furthermore, library design greatly contributes to the performance of the antibody selection process. For example, in phage display there is a limit to the number of phage that can be used in practical selection experiments, and the strategy chosen for library design and construction directly influences the percentage of functional clones in the library and the fraction of antibodies that are displayed on the phage as fusion to the minor coat protein pIII. Modular libraries, e.g. synthetic libraries based on conserved antibody scaffolds, may enable standardised affinity maturation procedures, thus facilitating the isolation of high affinity antibodies [7], which may be needed for diagnostic or therapeutic applications [8, 9, 10].

A number of possible combinatorial antibody libraries can be considered, for example those derived from antibody genes amplified from peripheral blood lymphocytes with suitable oligonucleotide primers [11, 12]. By contrast, synthetic antibody libraries are constructed in the laboratory using carefully designed antibody gene segments. Combinatorial mutagenesis of judiciously chosen amino acid positions can be used to construct such synthetic libraries.

Synthetic antibody libraries are particularly useful for practical pharmaceutical applications [11, 13, 14]. First, the antibody genes in these libraries have never undergone negative selection in vivo against antigens present in an organism. Secondly, the design of the library allows a careful control of the genetic structural elements, which can be introduced in the library. Third, library construction can use certain antibody genes that confer certain beneficial properties such as excellent stability, expression, low immunogenicity, tolerance to amino acids substitution, and performance in selections. Last but not least, certain antibody genes are characterised by the fact that the corresponding protein is capable of binding to protein A, thus facilitating the purification of corresponding antibody fragments by affinity chromatography.

The Neri group at ETH Zurich has previously designed, constructed and characterised a good quality human antibody library called ETH2-Gold library [13]. The ETH2-Gold library provides antibody fragments in single chain Fv (scFv) format. Each scFv consists of a heavy chain variable (VH) domain fused to a light chain variable (VL) domain, which may be either a VLκ or VLλ, domain. The library is characterised by an extremely high percentage of clones carrying full-length inserts (>98%), and may be expressed as scFv fused to the minor coat protein pIII of filamentous phage.

Within the scFv structure, the VH domains in the ETH2-Gold library are constructed on the basis of the DP47 VH germ line gene segment [15] on to which short diverse CDR3 loops have been appended by PCR reaction with partially degenerate primers. Similarly, the VL domains in the library consist either of a DPK22 germ line V kappa segment [16] or of a DPL16 germ line V lambda segment [17] on to which diverse CDR3 loops have been engineered by means of partially degenerate oligonucleotide primers.

The DP47 germ line VH segment is the most frequently used VH segment in humans [17]. Similarly DPK 22 and DPL 16 are often found in human antibodies [17]. The DP47 VH segment confers binding to protein A to the individual recombinant antibodies present in the ETH2-Gold library [18]. Furthermore, this VH segment is associated with a particularly good thermal stability [19]. The CDR3 loops of the VH and VL domains within the ETH2-Gold library were intentionally designed to be rather short. For example, the CDR3 loops of the VH domains contained either 4, 5 or 6 positions, which were combinatorially randomised. This strategy allowed the use of short, high quality oligonucleotides for CDR randomization and also limited the combinatorial diversity at the level of CDR3 loops, since such diversity could potentially generate antigenic determinants in vivo.

The ETH-2-Gold library can be used in a number of phage-based selection protocols, as well as in iterative colony filter screening experiments [1]. This library has proven over the years to be a rich source of antigen binding specificities yielding good quality human monoclonal antibodies against a variety of different targets. In addition, several human monoclonal antibodies have been generated against individual targets used as antigens for selections, yielding excellent paratope diversity (i.e., different antibody sequences binding to the same antigen).

However, we have recognised that paratope diversity per se does not guarantee epitope diversity. In other words, it can happen that human monoclonal antibodies generated from the same library are biased to recognise certain structural features within the target antigen of interest.

As described below, we have developed new antibody display libraries that retain the advantages of the synthetic ETH2-Gold library but allow selection of a different and/or greater diversity of epitope binding compared with ETH2-Gold.

We have developed two new libraries called Philo1 and Philo2, in which the CDR3 of the VH and VL domains are combinatorially mutated (as in ETH2-Gold) but a residue in the VH domain CDR2 is also mutated, for example position 52.

Before commenting further on the design, construction and characterisation of the Philo1 and Philo2 libraries it is worth considering certain useful structural features of the ETH2-Gold library that are commonly exploited for affinity maturation strategies. Moreover, it is worth analysing the role of CDR2 loops in library construction and performance.

An antibody antigen-binding site composed of a VH domain and a VL domain is typically formed by six loops of polypeptide: three from the VL and three from the VH. Analysis of antibodies of known atomic structure has elucidated relationships between the sequence and three-dimensional structure of antibody combining sites [20, 21]. These relationships imply that, except for the third region (loop) in VH domains, binding site loops have one of a small number of main-chain conformations: canonical structures. The canonical structure formed in a particular loop has been shown to be determined by its size and the presence of certain residues at key sites in both the loop and in framework regions [20, 21].

As mentioned before, the ETH2-Gold library is essentially based on two antibody scaffolds (one with a Vκ, one with a Vλ) on to which combinatorial immunogenesis at the level of CDR3 loops of both heavy and light chain has been performed. This modular design allows facile affinity maturation strategies after isolation of human monoclonal antibodies from the library. For example, affinity maturation may comprise combinatorial immunogenesis of CDR1 loops in the heavy and light chain, or simultaneous mutagenesis of CDR1 and CDR2 domains either in the heavy chain or in the light chain, thus yielding affinity maturation libraries which are likely to contain superior antigen binders [7, 22, 23, 24].

Experience has shown that the combinatorial mutagenesis of CDR1 loops in the heavy and light chain of recombinant antibodies isolated from the ETH2-Gold library is a particularly efficient strategy for the isolation of good quality high affinity human monoclonal antibodies [24]. One of the reasons behind the success of this affinity maturation strategy can be found in the relatively short nature of the CDR1 loops of DP47, DPK22 and DPL16. Indeed, when we analyse the structure and function of residues in the CDR1 loops of DP47, we can see that virtually only residues 30, 31, 32 and 33 are found in contact with protein antigens. Among these four positions, residues 31, 32 and 33 are more often found in contact with the target antigen. For this reason it is reasonable to combinatorially mutate the positions 31, 32 and 33 in affinity maturation libraries, thus restricting mutagenesis to the amino acid positions that are more likely to be in contact with the antigen.

Combinatorial mutagenesis of the CDR2 loop in the heavy chain is more difficult. In fact, positions between residue 50 and residue 58 have been found to contact antigen in three-dimensional structured determinations of antibody antigen complexes. Affinity maturation of a long CDR loop may require the use of long partially degenerate oligonucleotides for the simultaneous randomization of several positions within the same loop.

When using the ETH2-Gold library for the isolation of human monoclonal antibodies to antigens of interest, we can say that CDR3 loops compatible with antigen binding are isolated directly from the library in which these positions are combinatorially mutated. CDR1 loops in the heavy and light chains can be conveniently mutagenized in affinity maturation libraries, but certain positions of CDR2 loops in the heavy and light chain may bias the selection of the antibodies against the antigen of interest from the very beginning and thus influence the epitope which is recognised by the antibodies in the library.

The contribution of the VH domain for antigen recognition is thought to be more important than the role played by the VL domain in many cases, as revealed by the fact that greater combinatorial diversity is generated in vivo through VDJ recombination compared with the VJ recombination used for light chains, and also by the observation that functional antibodies exist which have only VH domains [25, 26].

Position 52 of VH CDR2 may be mutated in libraries of the invention. Within the CDR2 loops of VH domains in antibodies consisting of DP47 germ line segment [15], position 52 is often found in contact with the antigen. Amino acids in this position also occupy a central position within the antigen binding side whereas other positions in the loop—for example residue 54 or 56—are more peripheral.

The invention retains the advantages of the large, stable and highly diverse ETH2-Gold library of functional antibody molecules with similar physical properties, with sequence diversity restricted to the CDR3 loops which largely contribute to antigen recognition. However, the ability to explore a wider variety of epitopes compared with EHT2-Gold is made possible through mutation of a residue within the CDR2 of VH.

The new human combinatorial antibody libraries of the invention capitalize on our experience gained with the ETH2-Gold antibody library but include different amino acid residues at one position in the VH domain. These residues can be judiciously chosen to bias epitope recognition towards certain structural features that may not be compatible with antibody selections from the ETH2-Gold library.

These principles are exemplified in the Philo1 library, which has two charged amino acids (Lys or Asp) at position 52 in the VH CDR2, and in the Philo2 library, which has two amino acids capable of hydrogen bond formation (Asn or Tyr) at position 52 in the VH CDR2. In contrast, the ETH2-Gold library has the human DP47 germline Ser at this position.

The Philo1 and Philo2 libraries are both highly functional, each containing billions of antibody clones, with distinctive chemical features at position 52 which are still compatible with the highly efficient expression of stable single chain heavy fragments capable of protein A binding and capable of antigen recognition. The design of the library and its performance in selections against relevant antigens is described in the accompanying examples.

DETAILED DESCRIPTION OF THE INVENTION

The invention relates to advances in display libraries for selection of antibody molecules and provides improvements over the known library ETH2-Gold by providing alternative paratopes for selection and allows selection of antibody molecules for a greater diversity of antigen epitopes.

One aspect of the invention is a library of antibody molecules, wherein each antibody molecule comprises a VH domain consisting of a set of VH complementarity determining regions CDR1, CDR2 and CDR3, and framework regions, wherein the VH domain amino acid sequence corresponds to a human germline antibody heavy chain sequence in which a residue in VH CDR2, e.g. the residue at position 52 in VH CDR2, is mutated from germline and wherein residues in VH CDR3 are variably mutated.

By variably mutated it is meant that different antibody molecules in the library have different mutations at those residues. A residue position in the VH or VL domain is variably mutated if different residues are present at that position when the library is considered as a whole. For example there may be at least 2, at least 4, at least 10, at least 15 or at least 20 different residues at a variably mutated position in the library. The different residues at variably mutated positions may comprise non-germline residues, or in some cases may consist only of non-germline residues.

Figure 2:
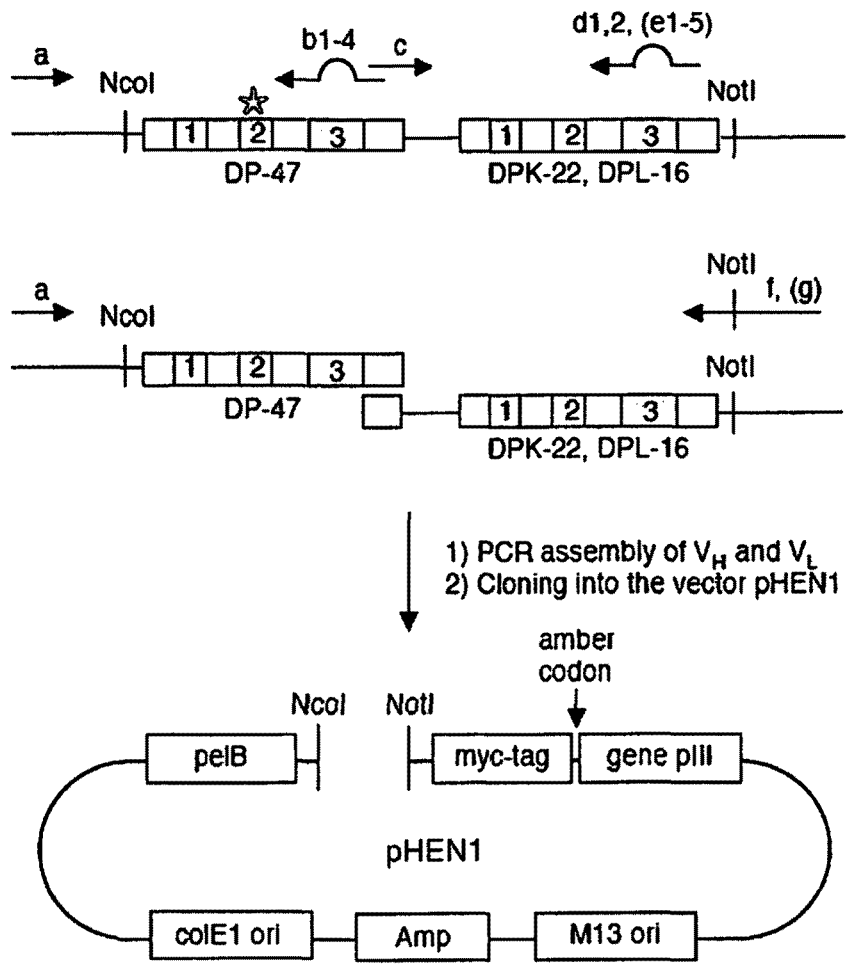
FIG. 2 illustrates the library cloning strategy. Mutations were introduced in the CDR3 regions by PCR using partially degenerate primers. Genes are indicated as rectangles and CDRs as numbered boxes. The VH and VL segment were then assembled by PCR and cloned into the pHen1 vector [18].

Variability may be achieved by random mutation of residues. Techniques such as site directed mutagenesis and error prone PCR may be used to produce variable mutation. A method described in the Examples herein is the generation of variable mutations by PCR using primers that anneal in the CDR3 region but contain variable oligonucleotide sequences corresponding to certain positions of CDR3, as illustrated in FIG. 2. Oligonucleotide primers may be used in which the codons corresponding to variably mutated residues are designed with the first two bases in each triplet being each selected from A, T, C and G, and the third base of each triplet selected from T and G only. Stop codons TAA and TGA are therefore not encoded. Examples of such primers are shown in Table 1 with codon MNN.

The invention also provides a library of antibody molecules wherein each antibody molecule comprises a VH domain, and optionally a VL domain forming a VH-VL domain pair, where sequence diversity in the VH complementarity determining regions is restricted to position 52 in CDR2 and to CDR3, and sequence diversity in the VL complementarity determining regions is restricted to CDR3. Other residues in the VH and VL domain CDRs may be germline residues and/or may be the same in all or most (e.g. at least 90%) of the antibody molecules in the library. VH and VL domain framework regions may be human germline framework regions.

Residues of antibody VH and VL domains are numbered using residue numbering according to Tomlinson [27] and as shown in the V-BASE database, which is currently available at http://vbase.mrc-cpe.cam.ac.uk.

A VH or VL domain framework comprises four framework regions, FR1, FR2, FR3 and FR4, interspersed with CDRs in the following structure:

FR1-CDR1-FR2-CDR2-FR3-CDR3-FR4

In human germline VH and VL domains, FR1, FR2 and FR3 correspond to a human germline v segment, e.g. DP47 for a VH domain, DPK22 or DPL16 for a VL domain, and FR4 corresponds to a human germline j segment, namely JH (e.g. JH4) for a VH domain, a JK segment for a VL Vκdomain, and a JL segment for a VL Vλ domain.

Position 52 of the VH domain falls within CDR2, and as explained above we have identified this position as one in which the nature of the amino acid residue may significantly bias the antigen binding specificity of the antibody molecule.

The ETH2-Gold library described previously is based on scFv with VH domains constructed from human germline DP47, in which CDR1 and CDR2 consist of germline residues and only the residues of CDR3 are variably mutated. Position 52 in the CDR2 of DP47 is the germline Ser residue. By mutating position 52 of CDR2 to be a non-germline residue in the present invention, we provide libraries of antibody molecules that are suitable for recognition of different antigen epitopes compared with those recognised by antibody molecules of ETH2-Gold.

In a library according to the invention, position 52 of VH CDR2 may be variably mutated. Thus, the library may have two or more different residues at position 52 in VH CDR2. For example position 52 may have two, or optionally more than two, non-germline residues at position 52. For example, residue 52 in VH CDR2 may be Asp (D) or Lys (K). As another example, residue 52 in VH CDR2 may be Asn (N) or Tyr (Y). Optionally, a library may have two or more different residues at position 52 in VH CDR2, wherein one of the residues at position 52 is a germline residue. For example, a library of the invention may comprise some VH domains in which residue 52 is a germline residue and some VH domains in which residue 52 is a non-germline residue. Thus, for DP47 VH domains, some VH domains may have Ser at position 52 and other domains may have a residue other than Ser. In some embodiments, all antibody molecules have a non-germline residue at position 52 of VH CDR2. A library of the invention may consist of antibody molecules in which position 52 in VH CDR2 is not Ser.

Optionally, VH domain within the library may comprise four different mutations at position 52 in VH CDR2. For example, position 52 may be a residue selected from Asn (N), Tyr (Y), Lys(K) or Asp (D).

It may be convenient to provide a library of antibody molecules in which the residues at position 52 of VH CDR2 are variably mutated but have similar character, e.g. charged, polar uncharged, or non-polar. For example, residues at position 52 may be charged (e.g. the library may have both positively charged and negatively charged residues at this position, or only positively charged residues, or only negatively charged residues). A library may have only charged residues at position 52, or may contain other residues as well. As another example, the library may have residues at position 52 that are capable of hydrogen bond formation, such as Asn (N) or Tyr (Y). Again, a library may have only residues capable of H-bond formation at position 52, or may contain other residues as well.

Positively charged amino acid residues include Lys (K) and Arg (R).

Negatively charged amino acid residues include Asp (D) and Glu (E).

His (H) is polar and may carry a positive or negative charge.

Polar uncharged amino acid residues include Asn (N), Tyr (Y), Ser (S), Thr (T), Glu (Q) and Cys (C).

Non polar amino acid residues include Gly (G), Ala (A), Val (V), Leu (L), Ile (I), Met (M), Pro (P), Phe (F) and Trp (W).

Any of the standard amino acids (including all those listed above) may be present in antibody molecules of the invention. Non-standard or uncommon residues (e.g. variants of standard residues) may also be present in some embodiments.

VH CDR3 consists of a sequence of residues numbered from 95 to 102. Numbering is non-linear since the length of the CDR is variable. There may be insertions after residue 100 which are numbered 100A, 100B, 100C etc. There may be deletions so that for example positions 99 and 100 are not present.

For example, VH CDR3 may be between 4 and 12 residues long, e.g. between 7 and 10 residues long, inclusive. As short CDR length allows convenient mutagenesis using oligonucleotides for CDR randomization, and reduces the risk of generating CDR loops that are immunogenic in vivo.

Any of the residues in VH CDR3 may be mutated. However, preferably the three residues preceding residue 103 in the VH domain are not mutated. Thus, these may be germline residues. Where all antibody molecules in the library have the same germline VH domain, these residues may therefore be the same in all antibody molecules. A VH domain may include a framework region corresponding to a JH4 human germline sequence, in which case these residues may be Phe, Asp and Tyr respectively.

At least four residues of VH CDR3 may be variably mutated, e.g. 4, 5, 6 or 7 residues. For example, VH CDR3 may contain sequences of variable residues (e.g. random sequences) of between 4 and 7 amino acids starting at position 95. Variable mutations may be present at any or all of positions 95, 96, 97, 98, 99 and 100 of VH CDR3, e.g. at residues 96, 97, 98 and 99.

As discussed in detail below, antibody molecules in the library may be whole immunoglobulin molecules or antibody fragments. Antibody molecules may comprise a VL domain in addition to a VH domain. An antibody VL domain consists of a set of VL complementarity determining regions CDR1, CDR2 and CDR3 and framework regions. Antibody molecules in the library may comprise a VH-VL domain pair.

The VL domain of an antibody molecule may correspond to a human germline antibody light chain in which residues in VL CDR3 are variably mutated. Two classes of human VL domains are known—Vκ and Vλ. Each VH domain in the library may be paired with a Vκ or a Vλ VL domain forming a VH-VL domain pair. An antibody library of the invention may include VL domains from either or both classes, i.e. all κ, all λ, or a mixture of κ and λ. A library may comprise VH-VL (Vκ) and VH-VL(Vλ) pairs, and there may be an approximately equal number of Vκ and Vλ domains in the library.

A Vκ domain may be a human germline DPK22 VL domain in which residues of VL CDR3 are variably mutated. A Vλ domain may be a human germline DPL16 VL domain in which residues of VL CDR3 are variably mutated.

VL CDR3 consists of a sequence of residues numbered from 89 to 97. Numbering is non-linear since the length of the CDR is variable. There may be insertions after residues 95 which are numbered 95A, 95B, 95C etc. In libraries of the invention, VL CDR3 may be between 4 and 12 residues long, e.g. 9, 10 or 11 residues long. For example, a CDR3 in a DPK22 VL domain may be 9 residues long. CDR3 in a DPL16 VL domain may be 11 residues long.

Any of the residues in VL CDR3 may be mutated. However, preferably residues 89 and 90 are not mutated, and therefore may be germline residues. Also, preferably residue 97 is not mutated, and may be germline. In a VA, domain e.g. DPL16, residues 91 and/or 96 may optionally not be variably mutated, e.g. residue 91 may be Ser and/or residue 96 may be germline.

A VL VκCDR3 domain may comprise a sequence of six residues starting at position 91, in which at least two, three, four or five residues are variably mutated. A VL Vλ CDR3 domain may comprise a sequence of six residues starting at position 92, in which at least two, three, four or five residues are variably mutated. For example, all six residues may be variably mutated (e.g. in a Vλ domain such as DPL16) or five of the six residues may be variably mutated, with the 5th residue in the sequence not variably mutated (e.g. in a Vκ domain such as DPK22). This 5th residue may be Pro.

Thus, a VL CDR3, e.g. a Vκ VL domain CDR3, may have Pro at this $5^{th}$ residue or at position 95. For example, at least 90 or 95% or all of K (e.g. DPK22) VL domain CDR3 sequences in a library may have Pro at this position. As exemplified in the Philo1 and Philo2 libraries detailed in the examples, we designed the CDR3 randomization of DPK22 so that a proline would fall in position 95 (we get a proline in position 95 in almost 100% of the cases), and a glycine in position 92 or 93 because this amino acid allows a turning in the loop structure thus reducing rigidity. Gly may also be present at these and/or other positions in other Vκ domain CDR3 sequences.

Thus, some (e.g. three, four or five) or all residues between positions 91 and 95, or some (e.g. three, four or five) or all residues between positions 91 and 96, of a VL Vκ CDR3 may be variably mutated.

Optionally, a VL domain CDR3 contains a Pro residue, e.g. a single Pro residue. Pro may be present in most (e.g. at least 90 or 95%) or all VL domain CDR3 sequences in the library.

In a human germline Vκ, e.g. DPK22, VL domain, CDR3 may be 9 residues long. Residues at positions 91, 92, 93, 94 and 96 may be variably mutated. Optionally, residue 92 and/or 93 is Gly. A library may therefore comprise Vκ, e.g.

DPK22, VL domains in which residue 92 is Gly, and DPK22 VL domains in which residue 93 is Gly.

A Pro residue may be present at position 95 in CDR3 of DPK22. Pro may be present at this position in some or all of the DPK22 Vκ domains in the library.

Residues 89 and 90 of the Vκ domain, e.g. DPK22, may be germline Gln. Residue 97 of the Vκ domain, e.g. DPK22, may be germline Thr.

In a human germline Vλ, e.g. DPL16, VL domain, CDR3 may be 11 residues long. Residues at positions 92, 93, 94, 95, 95A and 95B of VL CDR3 may be variably mutated. At least one of these residues may be Pro. For example, at least one of residues 92, 93, 94, 95A and 95B may be Pro. A library may comprise VL domains in which Pro is represented at all of these positions, in different VL domains. Thus, the library may comprise VL domains with Pro at 92, VL domains with Pro at 93, VL domains with Pro at 94, VL domains with Pro at 95A and VL domains with Pro at 95B. Optionally, a VL domain may contain Pro at only one of positions 92, 93, 94, 95A and 95B, e.g. it may have only one. Pro in CDR3.

Residues 90 of the Vλ domain, e.g. DPL16 may be germline Ser. Residue 91 of the Vλ domain, e.g. DPL16, may be Ser or may be a germline residue. Ser is a relatively small amino acid residue and its small size may be advantageous in allowing a variety of different amino acids to be accommodated at the variably mutated residues. Residues 96 and 97 of the Vλ domain, e.g. DPL16, may be germline Val.

FIG. 1B illustrates sequences of VH and VL domains of the invention, showing the residues mutated in VH and VL CDR3. Variable mutations may be present at any of the residue positions marked "X" in this figure.

Residues other than the variably mutated residues VH 52, VH CDR3 and VL CDR3 may be human germline residues. This does not, of course, exclude the possibility that the library will contain antibody molecules in which random errors in the sequence have resulted in accidental mutations from germline—such mutations occur naturally and typically arise by errors in DNA replication or in transcription or translation. Antibody molecules of the invention may therefore contain non-germline residues or mutations at positions other than those identified herein as being variably mutated, or that some antibody molecules in a library will contain residues that are different from those identified herein. However, it may be that in at least 90%, 95% or 99% of VH domains a library only the VH CDR3 residues and the residue in VH CDR2 are variably mutated and/or different from germline, and that in at least 90%, 95% or 99% of VL domains in a library only the VL CDR3 residues are variably mutated and/or different from germline.

Optionally, there may be other non-germline residues in the VH and/or VL domains. For example a VH or VL domain framework may have up to five, e.g. one, two or three non-germline residues in addition to the variably mutated residues. The same non-germline residue or residues in the VH and/or VL domain may optionally be present in all or most antibody molecules in the library, e.g. at least 90%, 95% or 99% of antibody molecules.

CDRs 1 and 2 (other than residue 52 in the VH domain) may consist of germline residues, though optionally a CDR1 and/or a CDR2 of the VH and/or VL domain may have other non-germline residues, e.g. may comprise one or two non-germline residues.

In antibody molecules of the invention, a VH domain may consist of a set of VH complementarity determining regions CDR1, CDR2 and CDR3, and framework regions, wherein the VH domain amino acid sequence consists of a human germline antibody heavy chain sequence in which there are up to twenty, up to fifteen or up to ten mutations from the germline sequence (e.g. insertions, deletions and/or substitution of non-germline residues), wherein a residue in VH CDR2, e.g. the residue at position 52 in VH CDR2, is mutated from germline and wherein residues in VH CDR3 are variably mutated.

In antibody molecules of the invention, a VL domain may consist of a set of VL complementarity determining regions CDR1, CDR2 and CDR3, and framework regions, wherein the VL domain amino acid sequence consists of a human germline antibody light chain sequence in which there are up to twenty, up to fifteen or up to ten mutations from the germline sequence (e.g. insertions, deletions and/or substitutions of non-germline residues), and wherein residues in VL CDR3 are variably mutated.

Antibody molecules in a library may comprise other sequences in addition to antibody sequences, for example antibody molecules may be conjugated as fusion proteins to linker peptides and/or peptide tags for purification, isolation or detection, and/or to polypeptides for display of the antibody molecules such as coat protein of filamentous phage as discussed in detail below. For example, a myc tag may be present, and may conveniently be fused to the end of the VL domain. The myc tag sequence AAAEQKLISEEDLNGAA (SEQ ID NO: 32) is shown in FIG. 1B. One or more spacer amino acids may be included e.g. to facilitate cloning and/or expression. For example, a Gly residue may be included at the C terminus of a VL domain. In the Philo1 and Philo2 libraries detailed in the Examples, Gly was included as a spacer residue between the DPL16 VL domain and the myc tag.

A library according to the invention may comprise in the order of $10^4$ antibody molecules upwards, for example at least $10^5$, at least $10^6$, at least $10^7$, at least $10^8$, at least $10^9$ or at least $10^{10}$ antibody molecules.

As illustrated in the Philo1 library described herein, a library according to the invention may comprise VH domains in which the residue at position 52 is Asp and VH domains in which the residue at position 52 is Lys. Optionally, all or most VH domains in the library have Asp or Lys at position 52. The VH domains may consist of the sequence:

```
[DP47 residues 1-51]              (SEQ ID NO: 22)]-

R52-[DP47 residues 53-94]         (SEQ ID NO: 23)]-

R95-R96-R97-R98-R99-R100-R100A-   SEQ ID NO: 24
``` wherein

R52 is Asp or Lys;

R95 is an amino acid;

R96 is an amino acid;

R97 is an amino acid;

R98 is an amino acid;

R99 is an amino acid or is not present;

R100 is an amino acid or is not present; and

R100A is an amino acid or is not present.

DP47 (V3-23) has the amino acid sequence shown below (SEQ ID NO: 25) with residue numbering, with CDRs 1 and 2 shown in square brackets, and with residue 52 of CDR2 boxed:

```
           1          2          3             4
  123456789012345678901234567890  12345  67890123456789
  EVQLLESGGGLVQPGGSLRLSCAASGFTFS [SYAMS] WVRQAPGKGLEWVS
                                  CDR1

5          6          7          8         9
  012a3456789012345 67890123456789012abc345678901234
  [AISGSGGSTYYADSVKG] RFTISRDNSKNTLYLQMNSLRAEDTAVYYCAK
          CDR2
```

The sequence and numbering above corresponds to that from the V-BASE database, currently available at http://vbase.mrc-cpe.cam.ac.uk.

SEQ ID NO: 22 is
EVQLLESGGGLVQPGGSLRLSCAASGFTFSSYAMSWVRQAPGKGLEWVSA I

This corresponds to residues 1-51 of DP47.

SEQ ID NO: 23 is
GSGGSTYYADSVKGRFTISRDNSKNTLYLQMNSLRAEDTAVYYCAK

This corresponds to residues 53-94 of DP47.

SEQ ID NO: 24 is
FDYWGQGTLVTVSS

This comprises a framework region corresponding to human germline gene segment JH4.

As illustrated in the Philo2 library described herein, a library according to the invention may comprise VH domains in which the residue at position 52 is Asn and VH domains in which the residue at position 52 is Tyr. Optionally, all or most VH domains in the library have Asn or Tyr at position 52. The VH domains may consist of the sequence:

[DP47 residues 1-51]            (SEQ ID NO: 22)]-

$R_{52}$-[DP47 residues 53-94]  (SEQ ID NO: 23)]-

$R_{95}$-$R_{96}$-$R_{97}$-$R_{98}$-$R_{99}$-$R_{100}$-$R_{100A}$-  SEQ ID NO: 24 wherein
$R_{52}$ is Asn or Tyr;
$R_{95}$ is an amino acid residue;
$R_{96}$ is an amino acid residue;
$R_{97}$ is an amino acid residue;
$R_{98}$ is an amino acid residue;
$R_{99}$ is an amino acid residue or is not present;
$R_{100}$ is an amino acid residue or is not present; and
$R_{100A}$ is an amino acid residue or is not present.

The above VH domains may be combined within a library, so that the library comprises VH domains with Asp, Lys, Asn or Tyr at position 52 in VH CDR2, i.e. in the above formula $R_{52}$ is Asp, Lys, Asn or Tyr.

As noted above, each of the DP47 VH domains may be paired with a DPK22 or DPL16 VL domain.

The DPK22 VL domain may consist of the sequence:

[DPK22 residues 1-90    (SEQ ID NO: 26)]-

$R_{91}$-$R_{92}$-$R_{93}$-$R_{94}$-Pro-$R_{96}$-  SEQ ID NO: 27 wherein
$R_{91}$, $R_{92}$, $R_{93}$, $R_{94}$ and $R_{96}$ are amino acid residues and wherein at least one of $R_{92}$ and $R_{93}$ is Gly.

DPK22 (Vκ3, A27) has the amino acid sequence shown below (SEQ ID NO: 28) with residue numbering, with CDRs shown in square brackets:

```
         1              2            3              4          5
  1234567890123456789 0123  45678901a234  567890123456789  0123456
  EIVLTQSPGTLSLSPGERATLSC [RASQSVSSSYLA] WYQQKPGQAPRLLIY [GASSRAT]
                           CDR1                          CDR2

6          7          8          9
  7890123456789012345678901 2345678  9012345
  GIPDRFSGSGSGTDFTLTISRLEPEDFAVYYC [QQYGSSP
                                    CDR3
```

The sequence and numbering above corresponds to that from the V-BASE database, currently available at the website located at the address vbase.mrc-cpe.cam.ac.uk.

SEQ ID NO: 26 is
EIVLTQSPGTLSLSPGERATLSCRASQSVSSSYLAWYQQKPGQAPRLLIY
GASSRATGIPDRFSGSGSGTDFTLTISRLEPEDFAVYYCQQ

This corresponds to residues 1-90 of DPK22.

SEQ ID NO: 27 is
TFGQGTKVEIK

This comprises a framework region corresponding to human germline gene segment JK1.

The DPL16 VL domain may consist of the sequence:

[DPL16 residues 1-90    (SEQ ID NO: 29)]-

$R_{91}$-$R_{92}$-$R_{93}$-$R_{94}$-$R_{95}$-$R_{95A}$-$R_{95B}$-  SEQ ID NO: 30 wherein
$R_{91}$, $R_{92}$, $R_{93}$, $R_{94}$, $R_{95}$, $R_{95A}$ and $R_{95B}$ are amino acid residues
wherein $R_{91}$ is Ser or Arg, preferably Ser
and wherein at least one of $R_{92}$, $R_{93}$, $R_{94}$ $R_{95A}$ and $R_{95B}$ is Pro.

DPL16 (VL3, 3 1) has the amino acid sequence shown below (SEQ ID NO: 31) with residue numbering, with CDRs shown in square brackets:

```
               2                3              4            5
12345678912345678901234 5678901234 567890123456789 0123456
SSELTQDPAVSVALGQTVRITC [QGDSLRSYYAS] WYQQKPGQAPVLVIY [GKNNRPS]
                        CDR1                       CDR2

6        7         8         9
78901234567890123456789012345678 9012345ab
GIPDRFSGSSSGNTASLTITGAQAEDEADYYC [NSRDSSGNH
                                 CDR3
```

The sequence and numbering above corresponds to that from the V-BASE database, currently available at the website located at the address vbase.mrc-cpe.cam.ac.uk.

SEQ ID NO: 29 is
SSELTQDPAVSVALGQTVRITCQGDSLRSYYASWYQQKPGQAPVLVIYGK

NNRPSGIPDRFSGSSSGNTASLTITGAQAEDEADYYCNS

This corresponds to residues 1-90 of DPL16.

SEQ ID NO: 30 is
VVFGGGTKLTVL

This comprises a framework region corresponding to human germline gene segment JL2 or JL3.

The Philo1 and Philo2 libraries may be combined to provide a single library with variable mutation of position 52 of VH CDR2 to Asp, Lys, Asn and Tyr.

A variety of different antigen-binding antibody molecules are known. Any suitable antibody molecule format may be used in a library of the invention. Antibody molecules may be whole antibodies, which have four polypeptide chains—two identical heavy chains and two identical light chains. The heavy and light chains form pairs, each having a VH-VL domain pair that contains an antigen binding site. The heavy and light chains also comprise constant regions: light chain CL, and heavy chain CH1, CH2, CH3 and sometimes CH4 (the fifth domain CH4 is present in human IgM and IgE). The two heavy chains are joined by disulphide bridges at a flexible hinge region.

Preferably, antibody molecules used in libraries of the invention are human antibody molecules. Thus, where constant domains are present these are preferably human constant domains.

Conveniently, antibody fragments and smaller antibody molecule formats, such as single chain antibody molecules, may be used in libraries according to the invention. For example, the antibody molecules may be scFv molecules, consisting of a VH domain and a VL domain joined by a linker peptide. In the scFv molecule, the VH and VL domains form a VH-VL pair in which the complementarity determining regions of the VH and VL come together to form an antigen binding site. A peptide GGGGSGGGGSGGGG (SEQ ID NO: 33) may link the VH and VL domain, as illustrated in FIG. 1B.

Other antibody fragments that comprise an antibody antigen-binding site include, but are not limited to, (i) the Fab fragment consisting of VL, VH, CL and CH1 domains; (ii) the Fd fragment consisting of the VH and CH1 domains; (iii) the Fv fragment consisting of the VL and VH domains of a single antibody; (iv) the dAb fragment [28, 29, 30], which consists of a VH or a VL domain; (v) isolated CDR regions; (vi) F(ab')$_2$ fragments, a bivalent fragment comprising two linked Fab fragments (vii) single chain Fv molecules (scFv), wherein a VH domain and a VL domain are linked by a peptide linker which allows the two domains to associate to form an antigen binding site [31, 32]; (viii) bispecific single chain Fv dimers (PCT/US92/09965) and (ix) "diabodies", multivalent or multispecific fragments constructed by gene fusion (WO94/13804; [33]). Fv, scFv or diabody molecules may be stabilized by the incorporation of disulphide bridges linking the VH and VL domains [34].

Various other antibody molecules including one or more antibody antigen-binding sites have been engineered, including for example Fab$_2$, Fab$_3$, diabodies, triabodies, tetrabodies and minibodies (small immune proteins). Antibody molecules and methods for their construction and use are described in [35].

Minibodies or small immune proteins (SIP) comprise scFv joined to a heavy chain constant domain CH3 and/or CH4 [36, 37]. For example, an antibody molecule may be an SIP comprising an scFv molecule fused to the CH4 domain of IgE.

Other examples of binding fragments are Fab', which differs from Fab fragments by the addition of a few residues at the carboxyl terminus of the heavy chain CH1 domain, including one or more cysteines from the antibody hinge region, and Fab'-SH, which is a Fab' fragment in which the cysteine residue(s) of the constant domains bear a free thiol group.

A dAb (domain antibody) is a small monomeric antigen-binding fragment of an antibody, namely the variable region of an antibody heavy or light chain [30]. VH dAbs occur naturally in camelids (e.g. camel, llama) and may be produced by immunizing a camelid with a target antigen, isolating antigen-specific B cells and directly cloning dAb genes from individual B cells. dAbs are also producible in cell culture. Their small size, good solubility and temperature stability makes them particularly physiologically useful and suitable for selection and affinity maturation. Camelid VH dAbs are being developed for therapeutic use under the name "Nanobodies™".

Synthetic antibody molecules may be created by expression from genes generated by means of oligonucleotides synthesized and assembled within suitable expression vectors, for example as described by Knappik et al. [38] or Krebs et al. [39].

Bispecific or bifunctional antibodies form a second generation of monoclonal antibodies in which two different variable regions are combined in the same molecule [40]. Their use has been demonstrated both in the diagnostic field and in the therapy field from their capacity to recruit new effector functions or to target several molecules on the surface of tumour cells. Where bispecific antibodies are to be used, these may be conventional bispecific antibodies, which can be manufactured in a variety of ways [41], e.g. prepared chemically or from hybrid hybridomas, or may be any of the bispecific antibody fragments mentioned above. These antibodies can be obtained by chemical methods [42, 43] or somatic methods [44, 45] but likewise and preferentially by genetic engineering techniques which allow the heterodimerization to be forced and thus facilitate the process of purification of the antibody sought [46]. Examples of bispecific antibodies include those of the BiTE™ technology in which the binding domains of two antibodies with different specificity can be used and directly linked via short flexible peptides. This combines two antibodies on a short single polypeptide chain. Diabodies and scFv can be constructed without an Fc region, using only variable domains, potentially reducing the effects of anti-idiotypic reaction.

Bispecific antibodies can be constructed as entire IgG, as bispecific Fab'2, as Fab'PEG, as diabodies or else as bispecific scFv. Further, two bispecific antibodies can be linked using routine methods known in the art to form tetravalent antibodies.

Bispecific diabodies, as opposed to bispecific whole antibodies, may also be particularly useful because they can be readily constructed and expressed in *E. coli*. Diabodies (and many other polypeptides, such as antibody fragments) of appropriate binding specificities can be readily selected e.g. using phage display. If one arm of the diabody is to be kept constant, for instance, with a specificity directed against an antigen of interest, then a library can be made where the other arm is varied and an antibody of appropriate specificity selected. Bispecific whole antibodies may be made by alternative engineering methods as described in Ridgeway et al., 1996 [47].

A library according to the invention may be used to select an antibody molecule that binds one or more antigens of interest. Selection from libraries is described in detail below. Following selection, the antibody molecule may then be engineered into a different format and/or to contain additional features. For example, the selected antibody molecule may be converted to a different format, such as one of the antibody formats described above. The selected antibody molecules, and antibody molecules comprising the VH and/or VL CDRs of the selected antibody molecules, are an aspect of the present invention. Antibody molecules and their encoding nucleic acid may be provided in isolated form.

Antibody fragments can be obtained starting from an antibody molecule by methods such as digestion by enzymes e.g. pepsin or papain and/or by cleavage of the disulphide bridges by chemical reduction. In another manner, the antibody fragments can be obtained by techniques of genetic recombination well known to the person skilled in the art or else by peptide synthesis by means of, for example, automatic peptide synthesizers, or by nucleic acid synthesis and expression.

It is possible to take monoclonal and other antibodies and use techniques of recombinant DNA technology to produce other antibodies or chimeric molecules that bind the target antigen. Such techniques may involve introducing DNA encoding the immunoglobulin variable region, or the CDRs, of an antibody to the constant regions, or constant regions plus framework regions, of a different immunoglobulin. See, for instance, EP-A-184187, GB 2188638A or EP-A-239400, and a large body of subsequent literature.

Antibody molecules may be selected from a library and then modified, for example the in vivo half life of an antibody molecule can be increased by chemical modification, for example PEGylation, or by incorporation in a liposome.

A library according to the invention may be screened for antibody molecules that bind one or more antigens of interest, and/or that bind a particular region or epitope of an antigen of interest.

The present invention provides a method of obtaining one or more antibody molecules able to bind an antigen, the method including bringing into contact a library of antibody molecules according to the invention and said antigen, and selecting one or more antibody molecules of the library able to bind said antigen.

A method may comprise:
providing a library of antibody molecules according to the invention, e.g. a bacterial library; and
contacting the library with the antigen, so that the antigen binds to one or more antibody molecules in the library; and
selecting nucleic acid encoding an antibody molecule that binds to the antigen.

The selecting step may comprise isolating the antibody molecule that is bound to the antigen, for example the antigen may be attached to magnetic beads or other molecules that may be recovered, thereby also recovering the antibody. The antibody molecule may be linked to its encoding nucleic acid, e.g. it may be part of a particle or replicable genetic package that contains the nucleic acid. Alternatively the selecting step may comprise isolating bacteria that express the antibody molecule, such as in the technique of iterative colony filter screening as described below. Nucleic acid encoding the antibody molecule that binds the antigen may then be isolated, if desired.

As discussed earlier, a variety of library formats and suitable screening methods are known.

A library of antibody molecules may be a bacterial library, e.g. *E. coli*. Thus, the antibody molecules may be expressed in bacteria. This may be achieved by providing bacteria containing nucleic acid molecules encoding the antibody molecules of the library, and culturing the bacteria so that they express the antibody molecules. Nucleic acid molecules encoding the antibody molecule library are an aspect of the invention, as are bacteria containing such nucleic acid. The bacteria may conveniently be stored as glycerol stocks.

Antibody molecules may be secreted from bacteria. This allows use of the technique of iterative colony filter screening (ICFS), a two-filter sandwich assay in which hundreds of millions of antibody-expressing bacterial colonies can be screened [1]. In ICFS, bacterial cells (typically *E. coli*) expressing the library are grown on a porous master filter in contact with a second filter coated with the antigen of interest. Antibody molecules are secreted by the bacteria and diffuse on to the second filter and thus are brought into contact with the antigen. Detection of antigen binding on the second filter allows the recovery of a number of bacterial cells, including those expressing the binding specificity of interest. In turn, those bacteria may be submitted to a second round of screening for the isolation of specific antibody molecules. Iteration of the steps refines the population of selected antibody molecules. Using this methodology, a number of specifically binding antibodies of different amino acid sequences may be recovered.

Alternatively, antibody molecules of a library may be displayed on particles or molecular complexes, rather than secreted. Suitable replicable genetic packages include yeast, bacterial or bacteriophage (e.g. T7) particles, viruses, cells or covalent, ribosomal or other in vitro display systems, each particle or molecular complex containing nucleic acid encoding the antibody VH variable domain displayed on it, and optionally also a displayed VL domain if present.

Selections using cells or protein mixtures have also been documented in the literature [48, 49, 50] and these techniques may be applied in the present invention.

Phage display is an established technique for selection of antibody molecules of desired specificity, in which the library of antibody molecules is displayed on filamentous bacteriophage [3, 11, 51]. Filamentous bacteriophage are viruses that infect bacteria, and thus the phage library may be maintained in a bacterial library. The antibody molecules may be fused to an inner coat protein pIII or to the major coat protein pVIII of the phage by inserting synthetic DNA encoding the peptide into phage gene III or gene VIII respectively. Three (or possibly five) copies of pIII are thought to be located at the tip of the phage particle and about 500 copies of pVIII are thought to be present per phage. pIII is responsible for attachment of the phage to the bacterial F-pilus and for infection, and pVIII is responsible for coating the single stranded phage DNA. The pIII protein has two domains. Fusions can be made to the N terminus of pIII or the N-terminal domain can be removed and fusions made to the second domain; however, phage lacking the N-terminal domain are not infective. A gene encoding scFv or other single chain antibody molecule can be inserted into gene III, resulting in expression of the antibody molecule fused to the N terminus of pIII and incorporated into the phage, allowing the phage to bind antigen. Dimeric antibody fragments, e.g. heterodimeric Fab, can be displayed by linking the heavy or light chain to a coat protein and secreting the other chain into the bacterial periplasm, where the two chains associate.

Nucleic acid molecules according to the invention may comprise a nucleotide sequence encoding an antibody molecule fused to a coat protein of filamentous bacteriophage, e.g. pIII or pVIII. Such nucleic acid molecules may be used either to express the library of antibody molecules displayed on phage that infect bacteria or to obtain soluble antibody secreted from the bacteria. By inserting an amber stop codon between the antibody molecule gene and the coat protein gene, when phage is grown in an amber suppressor strain of *E. coli* the amber codon is read as an amino acid and the antibody fused to the coat protein is displayed on the surface of the phage. When the phage is grown in a non-suppressor strain, the amber codon is read as a stop codon, and soluble protein is secreted from the bacteria. As illustrated in FIG. 1B, the amber codon may conveniently be included between sequences encoding a purification tag and the coat protein sequence, respectively.

Following selection of antibody molecules able to bind the antigen and displayed on bacteriophage or other library particles or molecular complexes, nucleic acid may be taken from the phage or other particle or molecular complex displaying a said selected antibody molecule. Such nucleic acid may be used in subsequent production of an antibody molecule or an antibody VH or VL variable domain by expression from nucleic acid with the sequence of nucleic acid taken from a bacteriophage or other particle or molecular complex displaying a said selected antibody molecule.

Thus, following selection, nucleic acid encoding the antibody molecule that binds the antigen may be expressed to produce the antibody molecule. Optionally the antibody molecule and/or its encoding nucleic acid may be subjected to further modifications, such as antibody reformatting as discussed elsewhere herein. The antibody molecule and/or its encoding nucleic acid may be formulated into compositions for therapeutic or diagnostic use. Thus, methods of the invention may comprise formulating an antibody molecule and/or its encoding nucleic acid into a composition comprising a pharmaceutically acceptable excipient, following isolation from the library and optional subsequent modifications.

Once one or more antibody molecules have been selected from the library, the antibody molecules may be further characterised to determine their properties in a variety of assays according to the purpose for which the antibody molecule is intended. Assays may include determining affinity of the antibody molecule for binding the antigen or antigens of interest, cross-reactivity with other antigens, epitope mapping to determine which region of an antigen is bound by the antibody molecule, immunohistochemistry, and other in vitro or in vivo tests. Certain steps in the antibody isolation procedure and in the downstream characterisation of binding specificities may be robotised, as described for the ETH2-Gold library [52].

EXAMPLES

Example 1

Design, Construction and Cloning of Philo1 and Philo2 Libraries

Figure 1:
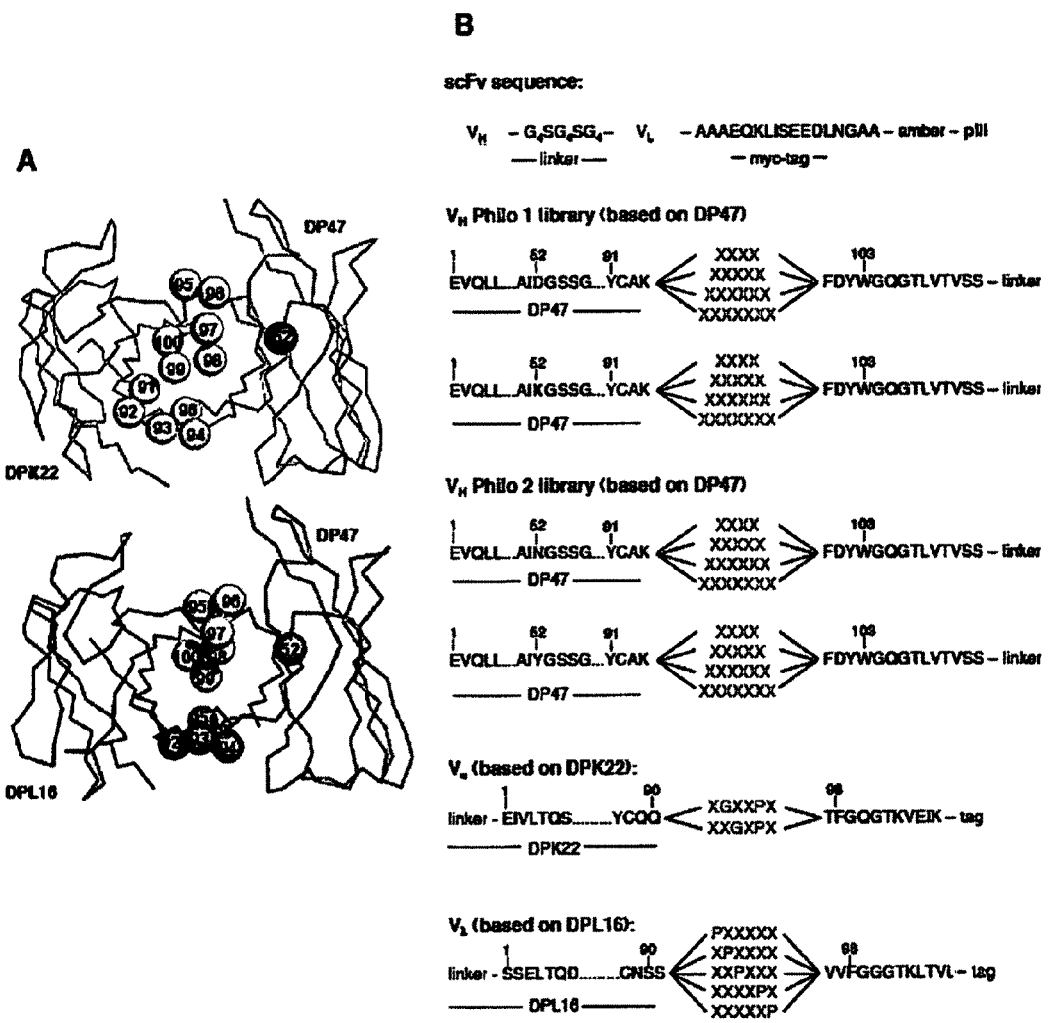
FIG. 1A shows the structure of DP47-DPK22(Vκ) (upper panel) and DP47-DPL16(Vλ) (lower panel) scFv. Residues subject to random mutation are DP47 CDR3 positions 95, 96, 97, 98, 99, 100 and 100A, DPK22 CDR3 position 91, 92, 93, 94 and 96 and DPL16 CDR3 position 92, 93, 94, 95 and 95A and 95B. Using the program PyMol the structure of the scFvs were modulated from the protein data base (Brookhaven Protein Data Bank) files 1igm and 8FAB for DP47-DPK22 and DP47-DPL16, respectively.
FIG. 1B shows the structure of the construct used to express the scFv for Philo1 and Philo2, and the randomised sequences of the Philo1 and Philo2 germline VH and VL domains.

We constructed synthetic antibody libraries in scFv format based on the ETH2-Gold library, restricting sequence diversity to the CDR3 of the variable heavy and light chain (VH and VL), which are known to largely contribute to antigen recognition, but also mutating a residue within the CDR2 of VH into either charged amino acids, such as D and K (Philo1 library) or polar/partially polar amino acids prone to hydrogen bond formation, i.e. N and Y (Philo2 library) (FIG. 1).

In our antibody libraries, residues are numbered according to Tomlinson et al. [27].

We introduced the point mutation at residue S52 of VH germline DP47 by PCR, using an ETH2-Gold clone as template and the primers: S52Dfo, S52Kfo, S52Nfo, S52Yfo (see Table I). The newly generated D-DP47 and K-DP47 were used as template for the heavy chain of the Philo1 library, N-DP47 and Y-DP47 were used for the Philo2 library (FIG. 1B).

The scFv antibody scaffold used for the library was based on the described DP47 segments coupled to either the variable lambda light chain (Vλ) DPL16 (FIG. 1A), or the variable kappa (Vκ) segment DPK22 (FIG. 1A) [15, 51, 53], which represent 12, 16, and 25%, respectively, of the antibody repertoire in humans [54]. The DP47 VH germline offers a number of advantages, ranging from higher thermodynamic stability [19] to the possibility of using Protein A for antibody purification and detection [55]. A flexible linker based on G4S repetition (GGGGSGGGGSGGGG) was used in both DP47/DPL16 and DP47/DPK22 pairs. Sequence variability in the variable heavy chain (VH) component of the library was introduced by PCR using partially degenerate primers (FIG. 2 and Table I), in a process that generates randomly mutated sequences of four to seven amino acid at positions 95-98. This short VH-CDR3 loop is followed by a conserved F-D-Y sequence (FIG. 1).

The variable light chain (VL) components of the library were generated in a similar fashion, introducing random mutations at positions 91, 92, 93, 94, and 96 in DPK22 CDR3 and at positions 92-95B in DPL16 CDR3 (FIG. 1 and FIG. 2 and Table I). For the K light chain domain, either residue 92 or 93 was engineered to be a glycine, whereas for the λ-light chain domain, at least one residue among positions 92, 93, 94, 95A and 95B was requested to be a proline.

VH-VL combinations were assembled in scFv format by PCR assembly (FIG. 2 and Table I), using gel-purified VH and VL segments as templates. The assembled VH-VL fragments were doubly-digested with NcoI/NotI and cloned into NcoI/NotI-digested pHEN1 phagemid vector [18]. Ninety μg of insert were ligated into 135 μg of vector and the resulting ligation product was electroporated into electrocompetent *Escherichia coli* TG1 cells [18, 56]. The eight sub-libraries were electroporated on eight different days respectively, thereby obtaining: Dλ, Dκ, Kλ, Kκ for Philo1 and Nλ, Nκ, Yλ, Yκ for Philo2, yielding to a total library size higher than 10⁹ individual clones. The libraries are stored as bacterial glycerol stocks.

Primers used in the amplification and assembly are listed in Table 1.

Example 2

Characterisation of Philo1 and Philo2

Figure 3:
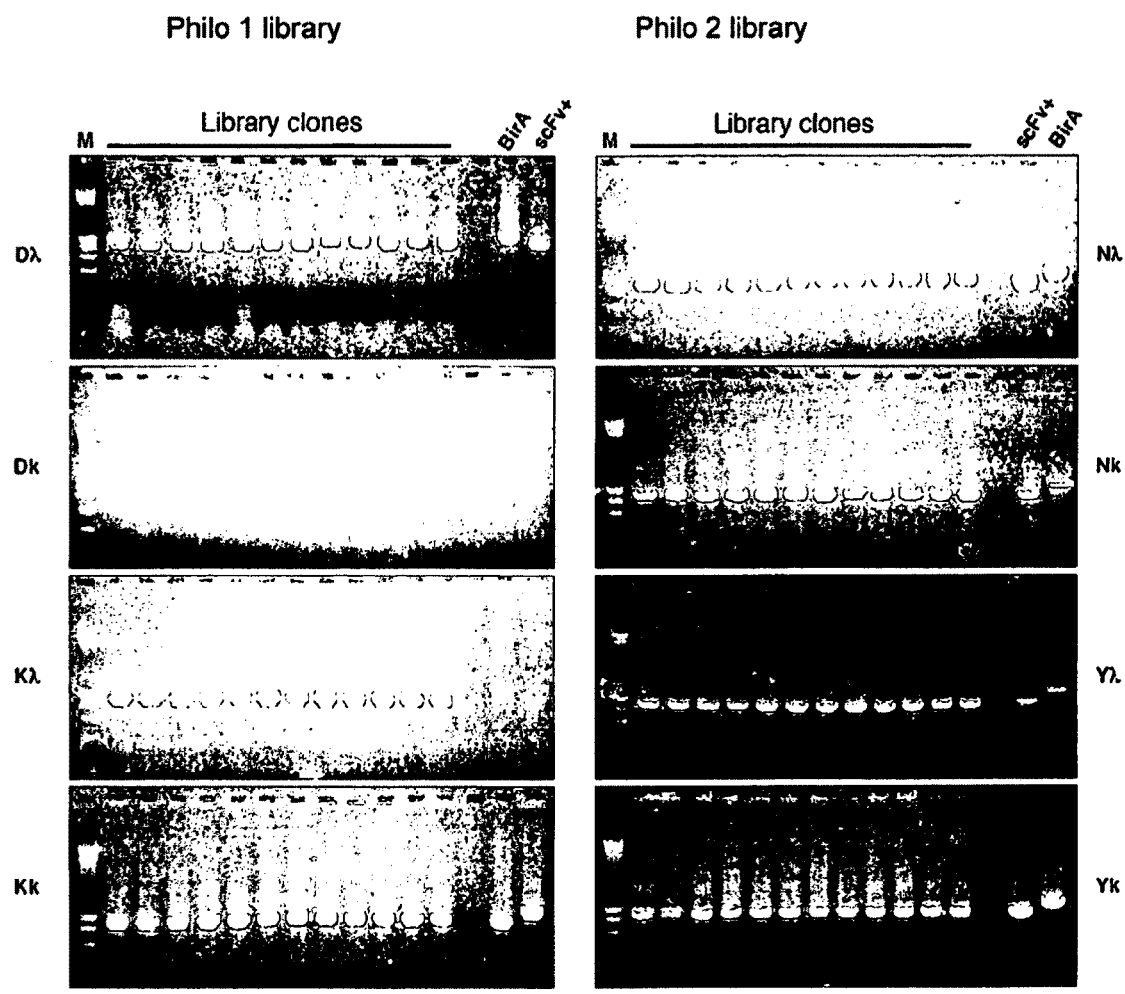
FIG. 3 illustrates PCR colony screening of 12 clones for each sub-library. In each gel, an amplified BirA insert (1200 bp) and scFv (approximately 1000 bp) in pHen1 vector were used as negative and positive controls respectively.

The quality and functionality of the library were assessed by PCR colony screening, dot blot, DNA sequencing and test selection against recombinant antigens. PCR screening was performed using the primers LMB3long and fdseqlong (Table1) and showed that all analyzed clones contained an insert of the correct size of approximately 1000 bp (FIG. 3). Twenty-four clones (three from each sub-library) were sequenced (Big Dye Terminator v1.1 Cycle Sequencing kit; ABI PRISM 3100 Genetic Analyzer) to check for the absence of frameshifts and of pervasive contaminations. All analysed clones showed different amino acid sequences in CDR3 of both heavy and light chains and no frameshift and no contamination.

Figure 4:
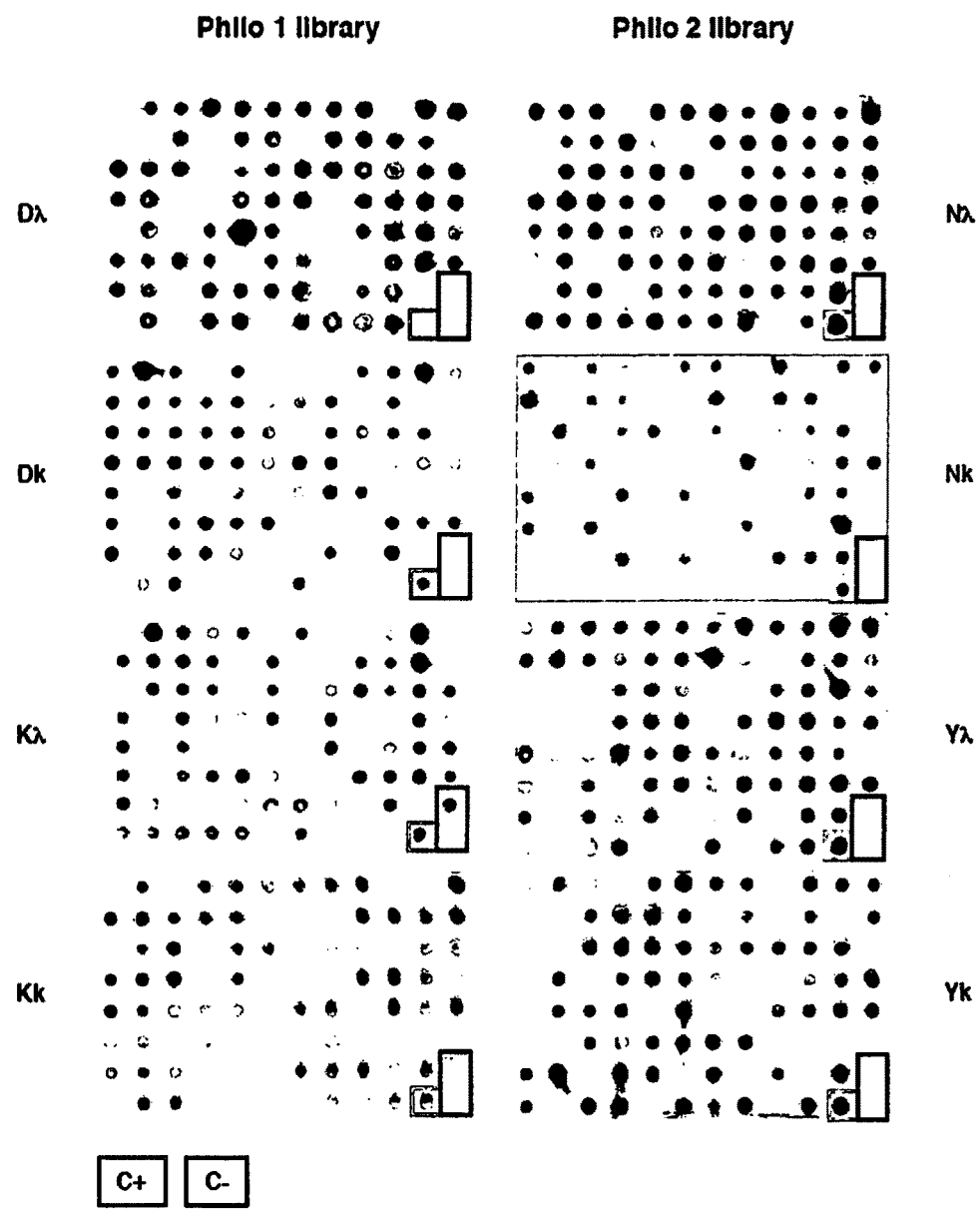
FIG. 4 shows dot blot analysis of more than 700 induced supernatants of individual library clones. Soluble scFv were detected with the mouse anti-myc tag mAb 9E10. More then 80% of the clones express a detectable amount of soluble scFv fragment. Each plate includes two negative controls (C−) and a positive control (C+). C+ was made using the supernatant of an ETH-2 GOLD clone which was known to efficiently express soluble scfv. C− was made using the simple growth medium 2YT+ampicillin+glucose without any inoculum, incubated at the same growth conditions as the other 96 clones.

The percentage of clones expressing soluble antibody fragments was determined by dot blot analysis of bacterial supernatants (ELIFA system; Perbio, Lausanne, Switzerland) using anti-myc mouse mAb 9E10 [51] and antimouse horseradish peroxidase immunoglobulins (Sigma-Aldrich; Buchs, Switzerland) as detecting reagents. Peroxidase activity was detected using the ECL plus Western blotting detection system (Amersham Biosciences). More than 80% of tested library clones expressed soluble scFv fragments (FIG. 4).

Example 3

Library Test Selection on Recombinant Antigens

All selections were performed using recombinant antigens with SDS-PAGE purity >90%. Immunotubes (Nunc, Germany) were coated with antigens at a concentration of 10-6 M in PBS overnight at room temperature. Immunotubes were then rinsed with PBS and blocked for 2 h at room temperature with 2% w/v skimmed milk in PBS (MPBS). After rinsing with PBS, 1012 phage particles in 2% MPBS were added to the immunotubes. The immunotubes were first incubated on a shaker for 30 min and then for 1.5 h standing upright at room temperature. Unbound phage was washed away by rinsing the immunotubes PBS 0.1% Tween 20 and with PBS. The bound phage was eluted in 1 mL of 100 mM triethylamine and inverting the tube for 5 min. Triethylamine was neutralized by adding 0.5 mL 1 M Tris-HCl pH 7.4. The eluted phage was used for the infection of exponentially growing *E. coli* TG1. More details about selection protocols can be found in Viti et al. [56].

Philo1 and Philo2 libraries were tested both separately and mixed together in selection experiments using a panel of different antigens: a tumor associated antigen from the murine tenascin C (a triple domain called mmBCD), Glutathion-S-transferase (GST) and a double domain of human nephrin (a protein of the renal filtration barrier, called nephrin 2-3).

Figure 5:
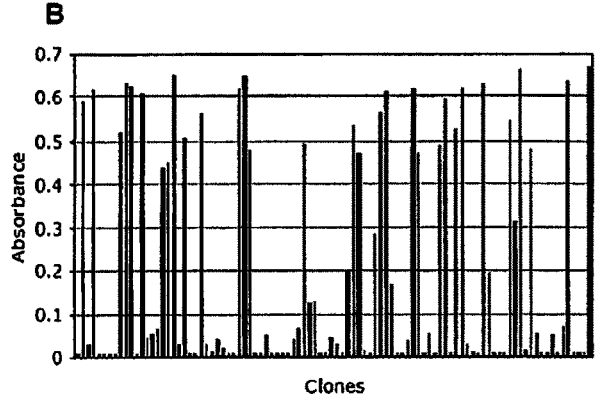
FIG. 5 shows selection from Philo1 and Philo2 separated libraries on standard recombinant antigens. Philo 1 was tested on a triple domain of murine tenascin C (mmBCD), a tumour associated antigen. Philo2 was tested on glutathion-s-transferase (GST) from *Schistosoma japunicum*. In panels A and C, the titres of bacterial colonies after the first and the second round of panning are shown. In panels B and D, results of ELISA performed on 92 induced supernatants from clones selected in the second round of panning are shown (absorbance at 450 nm).
Figure 5:
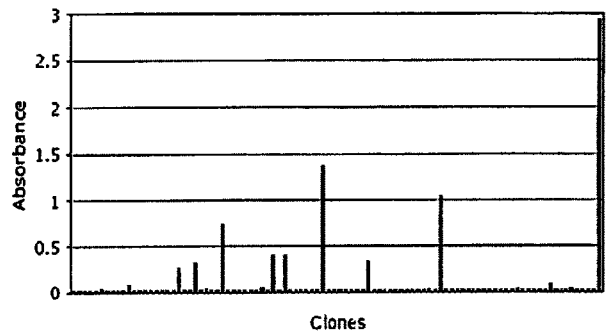

Philo1 library was tested on mmBCD and after the second round of panning ELISA assay was performed on 92 selected clones. More than 30 selected clones were able to give very strong absorbance signal (FIGS. 5A and B).

GST was used as antigen for Philo2 library testing. In this case after two rounds of panning 8 positive ELISA clones were found (FIGS. 5C and D).

Figure 6:
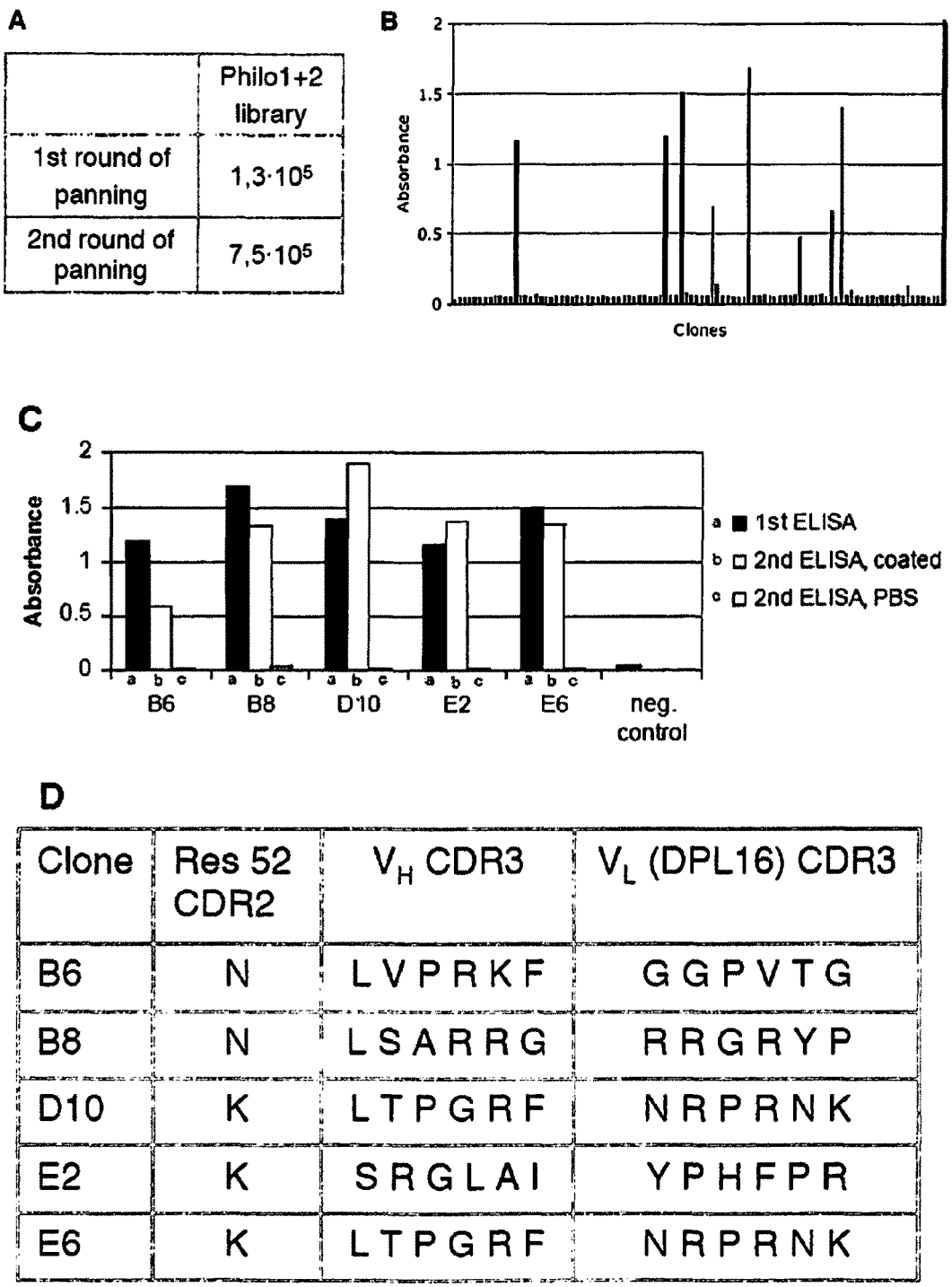
FIG. 6 shows selection from a combined Philo1+Philo2 library on a double domain of human nephrin (domain 2-3). A) Titre of bacterial colonies after the first and the second round of panning. B) Result (plot of absorbance at 450 nm) of ELISA performed on 92 induced supernatants from clones selected in the second round of panning. C) Plot of absorbance at 450 nm of specificity ELISA of 5 anti-nephrin clones. Columns "a" and "b" represent signals on nephrin-coated wells (performed in two different times), and column "c" represents signal on uncoated wells. D) Table of different CDR-sequences of different anti-nephrin selected clones (titre, ELISA, specificity ELISA and sequences) with Philo1+Philo2 together on the double domain2-3 of human nephrin.

We finally tested Philo1 and Philo2 library together on an antigen associated with the kidney filtration barrier and related to a disease known as congenital nephrotic syndrome of the Finnish type [57]. Eight strong positive clones were isolated after 2 rounds of panning (FIG. 6B) and tested for their specificity towards the antigen (FIG. 6C). Sequencing of 5 of the selected clones revealed four different sequences coming both from Philo1 library (clones D10=E6 and E2, with a K in position 52), and from Philo2 library (clones B6 and B8, bearing a N in position 52) (FIG. 6D).

Table 1

Sequence of primers used for the construction of the library. All primers used for the construction of the library were purchased from Operon Biotechnologies, Cologne, Germany.

Triplet MNN shown in the table below represents variably mutated codons. MNN is a codon that encodes an amino acid residue. In order to limit the probability of having STOP codons in the generated primer sequences, the first two positions of each codon were each selected from all four bases (A/T/G/C), while at the third position we used only G or T. This allowed all amino acids to be encoded but not the two stop codons TAA and TGA. The amber codon TAG can still be present, but we avoided this being read as a stop codon by using the TG1 bacterial strain which reads TAG as Gln instead of STOP.

(a) LMB3long

SEQ ID NO: 1

CAG GAA ACA GCT ATG ACC ATG ATT AC (b1) DP47CDR301fo

SEQ ID NO: 2

GT TCC CTG GCC CCA GTA GTC AAA MNN MNN MNN

MNN TTT CGC ACA GTA ATA TAC GGC C (b2) DP47CDR302fo

SEQ ID NO: 3

GT TCC CTG GCC CCA GTA GTC AAA MNN MNN MNN

MNN MNN TTT CGC ACA GTA ATA TAC GGC C (b3) DP47CDR303fo

SEQ ID NO: 4

GT TCC CTG GCC CCA GTA GTC AAA MNN MNN MNN

MNN MNN MNN TTT CGC ACA GTA ATA TAC GGC (b4) DP47CDR304fo

SEQ ID NO: 5

GT TCC CTG GCC CCA GTA GTC AAA MNN MNN MNN

MNN MNN MNN MNN TTT CGC ACA GTA ATA TAC GGC (c) DP47CDR3ba

SEQ ID NO: 6

TTT GAC TAC TGG GGC CAG GGA ACC CTG GTC (d1) DPK22CDR301fo

SEQ ID NO: 7

CAC CTT GGT CCC TTG GCC GAA CGT MNN CGG MNN

MNN ACC MNN CTG CTG ACA GTA ATA CAC TGC (d2) DPK22CDR302fo

SEQ ID NO: 8

CAC CTT GGT CCC TTG GCC GAA CGT MNN CGG MNN

ACC MNN MNN CTG CTG ACA GTA ATA CAC TGC

-continued (e1) DPL16CDR301ba
SEQ ID NO: 9
CTT GGT CCC TCC GCC GAA TAC CAC MNN MNN MNN

MNN MNN GGG AGA GGA GTT ACA GTA ATA GTC (e2) DPL16CDR302ba
SEQ ID NO: 10
CTT GGT CCC TCC GCC GAA TAC CAC MNN MNN MNN

MNN GGG MNN AGA GGA GTT ACA GTA ATA GTC (e3) DPL16CDR303ba
SEQ ID NO: 11
CTT GGT CCC TCC GCC GAA TAC CAC MNN MNN MNN

GGG MNN MNN AGA GGA GTT ACA GTA ATA GTC (e4) DPL16CDR304ba
SEQ ID NO: 12
CTT GGT CCC TCC GCC GAA TAC CAC MNN GGG MNN

MNN MNN MNN AGA GGA GTT ACA GTA ATA GTC (e5) DPL16CDR305ba
SEQ ID NO: 13
CTT GGT CCC TCC GCC GAA TAC CAC GGG MNN MNN

MNN MNN MNN AGA GGA GTT ACA GTA ATA GTC (f) DPK22FR4Not1fo
SEQ ID NO: 14
TCA TTC TCG ACT TGC GGC CGC TTT GAT TTC CAC

CTT GGT CCC TTG GCC GAA CG (g) DPL16FR4Not1fo
SEQ ID NO: 15
GAG TCA TTC TCG ACT TGC GGC CGC GCC TAG GAC

GGT CAG CTT GGT CCC TCC GCC GAA fdseqlong
SEQ ID NO: 16
GAC GTT AGT AAA TGA ATT TTC TGT ATG AGG S52Dfo
SEQ ID NO: 17
GC GTA GTA TGT GCT ACC ACC ACT ACC GTC AAT AGC

TGA GAC CCA CTC CAG

S52Kfo
SEQ ID NO: 18
GC GTA GTA TGT GCT ACC ACC ACT ACC CTT AAT AGC

TGA GAC CCA CTC CAG

S52Nfo
SEQ ID NO: 19
GC GTA GTA TGT GCT ACC ACC ACT ACC GTT AAT AGC

TGA GAC CCA CTC CAG

S52Yfo
SEQ ID NO: 20
GC GTA GTA TGT GCT ACC ACC ACT ACC ATA AAT AGC

TGA GAC CCA CTC CAG

S52ba
SEQ ID NO: 21
GGT AGT GGT GGT AGC ACA TAC TA

REFERENCES

1 Giovannoni et al., *Nucleic Acids Research*, 29, No. 5 e27 (2001)
2 Kuhne et al., *Journal of Clinical Microbiology*, 42, 2966-2976 (2004)
3 WO92/01047
4 Kontermann, R & Dubel, S, *Antibody Engineering*, Springer-Verlag New York, LLC; 2001, ISBN: 3540413545
5 Kawasaki U.S. Pat. Nos. 5,643,768 and 5,658,754
6 Griffiths, et al., *EMBO J.* 13 3245-3260 (1994)
7 Pini et al., *J. Biol. Chem.* 273 21769-21776 (1998)
8 Santimaria, et al., *Clin. Cancer Res.*, 9 571-579 (2003)
9 Chester, et al., *Cancer Chemother. Pharmacol.*, 46 Suppl, S8-S12 (2000)
10 Cooke, et al, *Bioconjug. Chem.* 13 7-15 (2002)
11 Winter et al. *Annu. Rev. Immunol.* 12, 433-455 (1994)
12 Vaughan et al. *Nat Biotechnol.* 14, 309-314 (1996)
13 Silacci et al. *Proteomics* 5(9): 2340-2350 (2005)
14 Rothe et al. *J Mol Biol*, 376, 1182-1200 (2008)
15 Tomlinson et al. *J Mol Bio*/227(3): 776-98 (1992)
16 Cox et al. *Eur J Immunol* 24(4): 827-36 (1994)
17 Griffiths et al. *Embo J* 13(14):3245-60 (1994)
18 Hoogenboom et al. *Nucleic Acids Res* 19(15):4133-4137 (1991)
19 Ewert et al. *J Mol Biol* 325(3): 531-53 (2003)
20 Chothia C. et al. *J Mol Biol* 227, 799-817 (1992)
21 Al-Lazikani, et al. *J Mol Biol* 273(4), 927-948 (1997)
22 Brack et al. *Clin Cancer Res.* 15; 12(10):3200-8 (2006)
23 Silacci et al. *Protein Eng Des Sel.* 19(10), 471-8. (2006)
24 Villa et al. *Int J Cancer* 122, 2405-2413 (2008)
25 Hamers-Casterman et al. *Nature* 363(6428): 446-8 (1993)
26 Ward, et al. *Nature* 341(6242): 544-6 (1989)
27 Tomlinson et al. *Embo J* 14(18):4628-4638 (1995)
28 Ward, E. S. et al., *Nature* 341, 544-546 (1989)
29 McCafferty et al *Nature*, 348, 552-554 (1990)
30 Holt et al *Trends in Biotechnology* 21, 484-490 (2003)
31 Bird et al, *Science*, 242, 423-426, (1988)
32 Huston et al, PNAS USA, 85, 5879-5883, (1988)
33 Holliger, P. et al, PNAS USA 90 6444-6448, (1993)
34 Reiter, Y. et al, *Nature Biotech*, 14, 1239-1245, (1996)
35 Holliger & Hudson, *Nature Biotechnology* 23(9):1126-1136 (2005)
36 Hu, S. et al, *Cancer Res.*, 56, 3055-3061, (1996)
37 Borsi et al. *Int. J. Cancer* 102, 75-85 (2002)
38 Knappik et al. *J. Mol. Biol.* 296, 57-86 (2000)
39 Krebs et al. *Journal of Immunological Methods* 254, 67-84 (2001)
40 Holliger and Bohlen *Cancer and metastasis rev.* 18: 411-419 (1999)
41 Holliger, P. and Winter G. *Current Opinion Biotechnol* 4, 446-449 (1993)
42 Glennie M J et al., *J. Immunol.* 139, 2367-2375 (1987)
43 Repp R. et al., *J. Hemat.* 377-382 (1995)
44 Staerz U. D. and Bevan M. J. *PNAS* 83 (1986)
45 Suresh M. R. et al., *Method Enzymol.* 121: 210-228 (1986)
46 Merchand et al., *Nature Biotech.* 16:677-681 (1998)
47 Ridgeway, J. B. B. et al, *Protein Eng.*, 9, 616-621, (1996)
48 Liu et al. *Cancer Res.* 64, 704-710 (2004)
49 Mutuberria et al. *J. Immunol. Methods* 287, 31-47 (2004)
50 Rubinstein et al. *Anal. Biochem.* 314, 294-300 (2003)
51 Marks et al. *J. Mol. Biol.* 222, 581-597 (1991)
52 Elia et al. *Trends Biotechnol.* 20, S19-S22 (2002)
53 Cox, Tomlinson et al. *Eur J. Immunol.* 24(4):827-836 1994
54 Griffiths, Williams et al. *EMBO J.* 13(14):3245-3260 1994
55 Hoogenboom and Winter *J Mol Biol* 227(2): 381-8 (1992)
56 Viti et al. *Methods Enzymol* 326: 480-505 (2000)
57 Holthofer et al. *Am J Pathol* 155(5): 1681-7 (1999)

The invention claimed is:

1. A library of antibody molecules, wherein each antibody molecule comprises a VH domain consisting of VH CDR1, CDR2 and CDR3 and framework regions, wherein the VH domain amino acid sequence corresponds to a human germline antibody heavy chain sequence in which the residue at position 52 in VH CDR2 is mutated from germline and wherein residues in VH CDR3 are variably mutated, said VH domain consisting of the sequence

SEQ ID NO: 22-

$R_{52}$- SEQ ID NO: 23-

$R_{95}$-$R_{96}$-$R_{97}$-$R_{98}$-$R_{99}$-$R_{100}$-$R_{100A}$- SEQ ID NO: 24 wherein $R_{52}$ is Asn or Tyr;

$R_{95}$ is an amino acid residue;

$R_{96}$ is an amino acid residue;

$R_{97}$ is an amino acid residue;

$R_{98}$ is an amino acid residue;

$R_{99}$ is an amino acid residue or is not present;

$R_{100}$ is an amino acid residue or is not present; and $R_{100A}$ is an amino acid residue or is not present.

2. A library according to claim 1, wherein residues at at least four positions in VH CDR3 are variably mutated.

3. A library according to claim 1, wherein VH CDR3 contains variable sequences of 4 to 7 amino acids starting at position 95.

4. A library according to claim 1, wherein the antibody molecules further comprise a VL domain, forming a VH-VL domain pair, wherein the VL domain consists of VL CDR1, CDR2 and CDR3 and framework regions.

5. A library of antibody molecules, wherein each antibody molecule comprises a VH domain consisting of VH CDR1, CDR2 and CDR3 and framework regions, wherein
the VH domain amino acid sequence corresponds to a human germline antibody heavy chain sequence in which the residue at position 52 in VH CDR2 is mutated from germline and wherein residues in VH CDR3 are variably mutated, said antibody molecules further comprising a DPK22 VL domain sequence of:

|  |  |
|---|---|
|  | SEQ ID NO: 26- |
| $R_{91}$-$R_{92}$-$R_{93}$-$R_{94}$-Pro-$R_{96}$- | SEQ ID NO: 27 | wherein $R_{91}$, $R_{92}$, $R_{93}$, $R_{94}$ and $R_{96}$ are amino acid residues and wherein at least one of $R_{92}$ and $R_{93}$ is Gly.

6. A library of claim 4, wherein the VL domain consists of the sequence:

|  |  |
|---|---|
|  | SEQ ID NO: 29- |
| $R_{91}$-$R_{92}$-$R_{93}$-$R_{94}$-$R_{95}$-$R_{95A}$-$R_{95B}$- | SEQ ID NO: 30 | wherein $R_{91}$, $R_{92}$, $R_{93}$, $R_{94}$, $R_{95}$, $R_{95A}$ and $R_{95B}$ are amino acid residues
wherein $R_{91}$ is Ser and wherein at least one of $R_{92}$, $R_{93}$, $R_{94}$, $R_{95A}$ and $R_{95B}$ is Pro.

7. A library according to claim 4, wherein the antibody molecules are scFv.

8. A method of selecting an antibody molecule that binds an antigen, comprising
providing a library according to claim 1; and
contacting the library with the antigen, so that the antigen binds to one or more antibody molecules in the library; and
selecting nucleic acid encoding an antibody molecule that binds to the antigen.

9. A method according to claim 8, comprising providing bacteria secreting the antibody molecules and performing iterative colony filter screening.

10. A method according to claim 8, further comprising expressing the nucleic acid to produce the antibody molecule, and isolating the antibody molecule.

11. A method according to claim 10, further comprising formulating the antibody molecule into a composition additionally comprising a pharmaceutically acceptable excipient.

12. A library according to claim 1, wherein the VH CDR1 and CDR2 consist of germline residues at positions other than residue 52.

13. A library according to claim 5, wherein residues at at least four positions in VH CDR3 are variably mutated.

14. A library according to claim 5, wherein VH CDR3 contains variable sequences of 4 to 7 amino acids starting at position 95.

15. A library according to claim 5, wherein the VH CDR1 and CDR2 consist of germline residues at positions other than residue 52.

16. A library according to claim 5 wherein said VH domain consists of the sequence

|  |  |
|---|---|
|  | SEQ ID NO: 22- |
| $R_{52}$- | SEQ ID NO: 23- |
| $R_{95}$-$R_{96}$-$R_{97}$-$R_{98}$-$R_{99}$-$R_{100}$-$R_{100A}$- | SEQ ID NO: 24 | wherein
$R_{52}$ is Asn or Tyr;
$R_{95}$ is an amino acid residue;
$R_{96}$ is an amino acid residue;
$R_{97}$ is an amino acid residue;
$R_{98}$ is an amino acid residue;
$R_{99}$ is an amino acid residue or is not present;
$R_{100}$ is an amino acid residue or is not present; and
$R_{100A}$ is an amino acid residue or is not present.

* * * * *

SEQUENCE LISTING

<160> NUMBER OF SEQ ID NOS: 63

<210> SEQ ID NO 1
<211> LENGTH: 26
<212> TYPE: DNA
<213> ORGANISM: Artificial sequence
<220> FEATURE:
<223> OTHER INFORMATION: Synthetic sequence: Primer LMB3long

<400> SEQUENCE: 1
caggaaacag ctatgaccat gattac                                          26

<210> SEQ ID NO 2
<211> LENGTH: 57
<212> TYPE: DNA
<213> ORGANISM: Artificial sequence
<220> FEATURE:
<223> OTHER INFORMATION: Synthetic sequence: Primer DP47CDR301fo
<220> FEATURE:
<221> NAME/KEY: misc_feature
<222> LOCATION: (25)..(26)
<223> OTHER INFORMATION: n is a/t/g/c
<220> FEATURE:
<221> NAME/KEY: misc_feature
<222> LOCATION: (28)..(29)
<223> OTHER INFORMATION: n is a/t/g/c
<220> FEATURE:
<221> NAME/KEY: misc_feature
<222> LOCATION: (31)..(32)
<223> OTHER INFORMATION: n is a/t/g/c
<220> FEATURE:
<221> NAME/KEY: misc_feature
<222> LOCATION: (34)..(35)
<223> OTHER INFORMATION: n is a/t/g/c

<400> SEQUENCE: 2
gttccctggc cccagtagtc aaamnnmnnm nnmnntttcg cacagtaata tacggcc       57

<210> SEQ ID NO 3
<211> LENGTH: 60
<212> TYPE: DNA
<213> ORGANISM: Artificial sequence
<220> FEATURE:
<223> OTHER INFORMATION: Synthetic sequence: Primer DP47CDR302fo
<220> FEATURE:
<221> NAME/KEY: misc_feature
<222> LOCATION: (25)..(26)
<223> OTHER INFORMATION: n is a/t/g/c
<220> FEATURE:
<221> NAME/KEY: misc_feature
<222> LOCATION: (28)..(29)
<223> OTHER INFORMATION: n is a/t/g/c
<220> FEATURE:
<221> NAME/KEY: misc_feature
<222> LOCATION: (31)..(32)
<223> OTHER INFORMATION: n is a/t/g/c
<220> FEATURE:
<221> NAME/KEY: misc_feature
<222> LOCATION: (34)..(35)
<223> OTHER INFORMATION: n is a/t/g/c
<220> FEATURE:
<221> NAME/KEY: misc_feature
<222> LOCATION: (37)..(38)
<223> OTHER INFORMATION: n is a/t/g/c

<400> SEQUENCE: 3
gttccctggc cccagtagtc aaamnnmnnm nnmnnmnntt tcgcacagta atatacggcc    60

<210> SEQ ID NO 4
<211> LENGTH: 62
<212> TYPE: DNA

```
<213> ORGANISM: Artificial sequence
<220> FEATURE:
<223> OTHER INFORMATION: Synthetic sequence: Primer DP47CDR303fo
<220> FEATURE:
<221> NAME/KEY: misc_feature
<222> LOCATION: (25)..(26)
<223> OTHER INFORMATION: n is a/t/g/c
<220> FEATURE:
<221> NAME/KEY: misc_feature
<222> LOCATION: (28)..(29)
<223> OTHER INFORMATION: n is a/t/g/c
<220> FEATURE:
<221> NAME/KEY: misc_feature
<222> LOCATION: (31)..(32)
<223> OTHER INFORMATION: n is a/t/g/c
<220> FEATURE:
<221> NAME/KEY: misc_feature
<222> LOCATION: (34)..(35)
<223> OTHER INFORMATION: n is a/t/g/c
<220> FEATURE:
<221> NAME/KEY: misc_feature
<222> LOCATION: (37)..(38)
<223> OTHER INFORMATION: n is a/t/g/c
<220> FEATURE:
<221> NAME/KEY: misc_feature
<222> LOCATION: (40)..(41)
<223> OTHER INFORMATION: n is a/t/g/c

<400> SEQUENCE: 4
gttccctggc cccagtagtc aaamnmnmnm nnmnmnmnmn ntttcgcaca gtaatatacg     60
gc                                                                  62

<210> SEQ ID NO 5
<211> LENGTH: 65
<212> TYPE: DNA
<213> ORGANISM: Artificial sequence
<220> FEATURE:
<223> OTHER INFORMATION: Synthetic sequence: Primer DP47CDR304fo
<220> FEATURE:
<221> NAME/KEY: misc_feature
<222> LOCATION: (25)..(26)
<223> OTHER INFORMATION: n is a/t/g/c
<220> FEATURE:
<221> NAME/KEY: misc_feature
<222> LOCATION: (28)..(29)
<223> OTHER INFORMATION: n is a/t/g/c
<220> FEATURE:
<221> NAME/KEY: misc_feature
<222> LOCATION: (31)..(32)
<223> OTHER INFORMATION: n is a/t/g/c
<220> FEATURE:
<221> NAME/KEY: misc_feature
<222> LOCATION: (34)..(35)
<223> OTHER INFORMATION: n is a/t/g/c
<220> FEATURE:
<221> NAME/KEY: misc_feature
<222> LOCATION: (37)..(38)
<223> OTHER INFORMATION: n is a/t/g/c
<220> FEATURE:
<221> NAME/KEY: misc_feature
<222> LOCATION: (40)..(41)
<223> OTHER INFORMATION: n is a/t/g/c
<220> FEATURE:
<221> NAME/KEY: misc_feature
<222> LOCATION: (43)..(44)
<223> OTHER INFORMATION: n is a/t/g/c

<400> SEQUENCE: 5
gttccctggc cccagtagtc aaamnmnmnm nmnmnmnmn nmntttcgc acagtaatat      60 acggc                                                               65

<210> SEQ ID NO 6
<211> LENGTH: 30
<212> TYPE: DNA
```

<213> ORGANISM: Artificial sequence
<220> FEATURE:
<223> OTHER INFORMATION: Synthetic sequence: Primer DP47CDR3ba

<400> SEQUENCE: 6
tttgactact ggggccaggg aaccctggtc                                           30

<210> SEQ ID NO 7
<211> LENGTH: 63
<212> TYPE: DNA
<213> ORGANISM: Artificial sequence
<220> FEATURE:
<223> OTHER INFORMATION: Synthetic sequence: Primer DPK22CDR301fo
<220> FEATURE:
<221> NAME/KEY: misc_feature
<222> LOCATION: (26)..(27)
<223> OTHER INFORMATION: n is a/t/g/c
<220> FEATURE:
<221> NAME/KEY: misc_feature
<222> LOCATION: (32)..(33)
<223> OTHER INFORMATION: n is a/t/g/c
<220> FEATURE:
<221> NAME/KEY: misc_feature
<222> LOCATION: (35)..(36)
<223> OTHER INFORMATION: n is a/t/g/c
<220> FEATURE:
<221> NAME/KEY: misc_feature
<222> LOCATION: (41)..(42)
<223> OTHER INFORMATION: n is a/t/g/c

<400> SEQUENCE: 7
caccttggtc ccttggccga acgtmnncgg mnnmnnaccm nnctgctgac agtaatacac          60
tgc                                                                       63

<210> SEQ ID NO 8
<211> LENGTH: 63
<212> TYPE: DNA
<213> ORGANISM: Artificial sequence
<220> FEATURE:
<223> OTHER INFORMATION: Synthetic sequence: Primer DPK22CDR302fo
<220> FEATURE:
<221> NAME/KEY: misc_feature
<222> LOCATION: (26)..(27)
<223> OTHER INFORMATION: n is a/t/g/c
<220> FEATURE:
<221> NAME/KEY: misc_feature
<222> LOCATION: (32)..(33)
<223> OTHER INFORMATION: n is a/t/g/c
<220> FEATURE:
<221> NAME/KEY: misc_feature
<222> LOCATION: (38)..(39)
<223> OTHER INFORMATION: n is a/t/g/c
<220> FEATURE:
<221> NAME/KEY: misc_feature
<222> LOCATION: (41)..(42)
<223> OTHER INFORMATION: n is a/t/g/c

<400> SEQUENCE: 8
caccttggtc ccttggccga acgtmnncgg mnnaccmnnm nnctgctgac agtaatacac          60
tgc                                                                       63

<210> SEQ ID NO 9
<211> LENGTH: 63
<212> TYPE: DNA
<213> ORGANISM: Artificial sequence
<220> FEATURE:
<223> OTHER INFORMATION: Synthetic sequence: Primer DPL16CDR301ba
<220> FEATURE:
<221> NAME/KEY: misc_feature
<222> LOCATION: (26)..(27)
<223> OTHER INFORMATION: n is a/t/g/c
<220> FEATURE:

```
<221> NAME/KEY: misc_feature
<222> LOCATION: (29)..(30)
<223> OTHER INFORMATION: n is a/t/g/c
<220> FEATURE:
<221> NAME/KEY: misc_feature
<222> LOCATION: (32)..(33)
<223> OTHER INFORMATION: n is a/t/g/c
<220> FEATURE:
<221> NAME/KEY: misc_feature
<222> LOCATION: (35)..(36)
<223> OTHER INFORMATION: n is a/t/g/c
<220> FEATURE:
<221> NAME/KEY: misc_feature
<222> LOCATION: (38)..(39)
<223> OTHER INFORMATION: n is a/t/g/c

<400> SEQUENCE: 9
cttggtccct ccgccgaata ccacmnnmnn mnnmnnmnng ggagaggagt tacagtaata      60
gtc                                                                  63

<210> SEQ ID NO 10
<211> LENGTH: 63
<212> TYPE: DNA
<213> ORGANISM: Artificial sequence
<220> FEATURE:
<223> OTHER INFORMATION: Synthetic sequence: Primer DPL16CDR302ba
<220> FEATURE:
<221> NAME/KEY: misc_feature
<222> LOCATION: (26)..(27)
<223> OTHER INFORMATION: n is a/t/g/c
<220> FEATURE:
<221> NAME/KEY: misc_feature
<222> LOCATION: (29)..(30)
<223> OTHER INFORMATION: n is a/t/g/c
<220> FEATURE:
<221> NAME/KEY: misc_feature
<222> LOCATION: (32)..(33)
<223> OTHER INFORMATION: n is a/t/g/c
<220> FEATURE:
<221> NAME/KEY: misc_feature
<222> LOCATION: (35)..(36)
<223> OTHER INFORMATION: n is a/t/g/c
<220> FEATURE:
<221> NAME/KEY: misc_feature
<222> LOCATION: (41)..(42)
<223> OTHER INFORMATION: n is a/t/g/c

<400> SEQUENCE: 10
cttggtccct ccgccgaata ccacmnnmnn mnnmnngggm nnagaggagt tacagtaata     60
gtc                                                                  63

<210> SEQ ID NO 11
<211> LENGTH: 63
<212> TYPE: DNA
<213> ORGANISM: Artificial sequence
<220> FEATURE:
<223> OTHER INFORMATION: Synthetic sequence: Primer DPL16CDR303ba
<220> FEATURE:
<221> NAME/KEY: misc_feature
<222> LOCATION: (26)..(27)
<223> OTHER INFORMATION: n is a/t/g/c
<220> FEATURE:
<221> NAME/KEY: misc_feature
<222> LOCATION: (29)..(30)
<223> OTHER INFORMATION: n is a/t/g/c
<220> FEATURE:
<221> NAME/KEY: misc_feature
<222> LOCATION: (32)..(33)
<223> OTHER INFORMATION: n is a/t/g/c
<220> FEATURE:
<221> NAME/KEY: misc_feature
<222> LOCATION: (38)..(39)
<223> OTHER INFORMATION: n is a/t/g/c
<220> FEATURE:
```

<221> NAME/KEY: misc_feature
<222> LOCATION: (41)..(42)
<223> OTHER INFORMATION: n is a/t/g/c

<400> SEQUENCE: 11
cttggtccct ccgccgaata ccacmnnmnn mnngggmnnm nnagaggagt tacagtaata    60
gtc                                                                 63

<210> SEQ ID NO 12
<211> LENGTH: 63
<212> TYPE: DNA
<213> ORGANISM: Artificial sequence
<220> FEATURE:
<223> OTHER INFORMATION: Synthetic sequence: Primer DPL16CDR304ba
<220> FEATURE:
<221> NAME/KEY: misc_feature
<222> LOCATION: (26)..(27)
<223> OTHER INFORMATION: n is a/t/g/c
<220> FEATURE:
<221> NAME/KEY: misc_feature
<222> LOCATION: (32)..(33)
<223> OTHER INFORMATION: n is a/t/g/c
<220> FEATURE:
<221> NAME/KEY: misc_feature
<222> LOCATION: (35)..(36)
<223> OTHER INFORMATION: n is a/t/g/c
<220> FEATURE:
<221> NAME/KEY: misc_feature
<222> LOCATION: (38)..(39)
<223> OTHER INFORMATION: n is a/t/g/c
<220> FEATURE:
<221> NAME/KEY: misc_feature
<222> LOCATION: (41)..(42)
<223> OTHER INFORMATION: n is a/t/g/c

<400> SEQUENCE: 12
cttggtccct ccgccgaata ccacmnnggg mnnmnmnmnm nnagaggagt tacagtaata    60
gtc                                                                 63

<210> SEQ ID NO 13
<211> LENGTH: 63
<212> TYPE: DNA
<213> ORGANISM: Artificial sequence
<220> FEATURE:
<223> OTHER INFORMATION: Synthetic sequence: Primer DPL16CDR305ba
<220> FEATURE:
<221> NAME/KEY: misc_feature
<222> LOCATION: (29)..(30)
<223> OTHER INFORMATION: n is a/t/g/c
<220> FEATURE:
<221> NAME/KEY: misc_feature
<222> LOCATION: (32)..(33)
<223> OTHER INFORMATION: n is a/t/g/c
<220> FEATURE:
<221> NAME/KEY: misc_feature
<222> LOCATION: (35)..(36)
<223> OTHER INFORMATION: n is a/t/g/c
<220> FEATURE:
<221> NAME/KEY: misc_feature
<222> LOCATION: (38)..(39)
<223> OTHER INFORMATION: n is a/t/g/c
<220> FEATURE:
<221> NAME/KEY: misc_feature
<222> LOCATION: (41)..(42)
<223> OTHER INFORMATION: n is a/t/g/c

<400> SEQUENCE: 13
cttggtccct ccgccgaata ccacgggmnn mnnmnmnmnm nnagaggagt tacagtaata    60
gtc                                                                 63

<210> SEQ ID NO 14

```
<211> LENGTH: 53
<212> TYPE: DNA
<213> ORGANISM: Artificial sequence
<220> FEATURE:
<223> OTHER INFORMATION: Synthetic sequence: Primer DPK22FR4NotIfo

<400> SEQUENCE: 14
tcattctcga cttgcggccg ctttgatttc caccttggtc ccttggccga acg          53

<210> SEQ ID NO 15
<211> LENGTH: 57
<212> TYPE: DNA
<213> ORGANISM: Artificial sequence
<220> FEATURE:
<223> OTHER INFORMATION: Synthetic sequence: Primer DPL16FR4NotIfo

<400> SEQUENCE: 15
gagtcattct cgacttgcgg ccgcgcctag gacggtcagc ttggtccctc cgccgaa      57

<210> SEQ ID NO 16
<211> LENGTH: 30
<212> TYPE: DNA
<213> ORGANISM: Artificial sequence
<220> FEATURE:
<223> OTHER INFORMATION: Synthetic sequence: Primer fdseqlong

<400> SEQUENCE: 16
gacgttagta aatgaatttt ctgtatgagg                                    30

<210> SEQ ID NO 17
<211> LENGTH: 50
<212> TYPE: DNA
<213> ORGANISM: Artificial sequence
<220> FEATURE:
<223> OTHER INFORMATION: Synthetic sequence: Primer S52Dfo

<400> SEQUENCE: 17
gcgtagtatg tgctaccacc actaccgtca atagctgaga cccactccag              50

<210> SEQ ID NO 18
<211> LENGTH: 50
<212> TYPE: DNA
<213> ORGANISM: Artificial sequence
<220> FEATURE:
<223> OTHER INFORMATION: Synthetic sequence: Primer S52Kfo

<400> SEQUENCE: 18
gcgtagtatg tgctaccacc actaccctta atagctgaga cccactccag              50

<210> SEQ ID NO 19
<211> LENGTH: 50
<212> TYPE: DNA
<213> ORGANISM: Artificial sequence
<220> FEATURE:
<223> OTHER INFORMATION: Synthetic sequence: Primer S52Nfo

<400> SEQUENCE: 19
gcgtagtatg tgctaccacc actaccgtta atagctgaga cccactccag              50

<210> SEQ ID NO 20
<211> LENGTH: 50
<212> TYPE: DNA
<213> ORGANISM: Artificial sequence
<220> FEATURE:
<223> OTHER INFORMATION: Synthetic sequence: Primer S52Yfo

<400> SEQUENCE: 20
```

```
gcgtagtatg tgctaccacc actaccataa atagctgaga cccactccag          50
```

<210> SEQ ID NO 21
<211> LENGTH: 23
<212> TYPE: DNA
<213> ORGANISM: Artificial sequence
<220> FEATURE:
<223> OTHER INFORMATION: Synthetic sequence: Primer S52ba

<400> SEQUENCE: 21

```
ggtagtggtg gtagcacata cta                                      23
```

<210> SEQ ID NO 22
<211> LENGTH: 51
<212> TYPE: PRT
<213> ORGANISM: Homo sapiens

<400> SEQUENCE: 22

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile
    50
```

<210> SEQ ID NO 23
<211> LENGTH: 46
<212> TYPE: PRT
<213> ORGANISM: Homo sapiens

<400> SEQUENCE: 23

```
Gly Ser Gly Gly Ser Thr Tyr Tyr Ala Asp Ser Val Lys Gly Arg Phe
1               5                   10                  15

Thr Ile Ser Arg Asp Asn Ser Lys Asn Thr Leu Tyr Leu Gln Met Asn
            20                  25                  30

Ser Leu Arg Ala Glu Asp Thr Ala Val Tyr Tyr Cys Ala Lys
        35                  40                  45
```

<210> SEQ ID NO 24
<211> LENGTH: 14
<212> TYPE: PRT
<213> ORGANISM: Homo sapiens

<400> SEQUENCE: 24

```
Phe Asp Tyr Trp Gly Gln Gly Thr Leu Val Thr Val Ser Ser
1               5                   10
```

<210> SEQ ID NO 25
<211> LENGTH: 98
<212> TYPE: PRT
<213> ORGANISM: Homo sapiens

<400> SEQUENCE: 25

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Ser Gly Ser Gly Gly Ser Thr Tyr Tyr Ala Asp Ser Val
```

```
                    50                  55                  60
Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                 85                  90                  95

Ala Lys

<210> SEQ ID NO 26
<211> LENGTH: 91
<212> TYPE: PRT
<213> ORGANISM: Homo sapiens

<400> SEQUENCE: 26

Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
                 20                  25                  30

Tyr Leu Ala Trp Tyr Gln Gln Lys Pro Gly Gln Ala Pro Arg Leu Leu
                 35                  40                  45

Ile Tyr Gly Ala Ser Ser Arg Ala Thr Gly Ile Pro Asp Arg Phe Ser
             50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln
                 85                  90

<210> SEQ ID NO 27
<211> LENGTH: 11
<212> TYPE: PRT
<213> ORGANISM: Homo sapiens

<400> SEQUENCE: 27

Thr Phe Gly Gln Gly Thr Lys Val Glu Ile Lys
  1               5                  10

<210> SEQ ID NO 28
<211> LENGTH: 96
<212> TYPE: PRT
<213> ORGANISM: Homo sapiens

<400> SEQUENCE: 28

Glu Ile Val Leu Thr Gln Ser Pro Gly Thr Leu Ser Leu Ser Pro Gly
  1               5                  10                  15

Glu Arg Ala Thr Leu Ser Cys Arg Ala Ser Gln Ser Val Ser Ser Ser
                 20                  25                  30

Tyr Leu Ala Trp Tyr Gln Gln Lys Pro Gly Gln Ala Pro Arg Leu Leu
                 35                  40                  45

Ile Tyr Gly Ala Ser Ser Arg Ala Thr Gly Ile Pro Asp Arg Phe Ser
             50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Tyr Gly Ser Ser Pro
                 85                  90                  95

<210> SEQ ID NO 29
<211> LENGTH: 89
<212> TYPE: PRT
<213> ORGANISM: Homo sapiens

<400> SEQUENCE: 29
```

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
                20                  25                  30

Ser Trp Tyr Gln Gln Lys Pro Gly Gln Ala Pro Val Leu Val Ile Tyr
            35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser
                85

<210> SEQ ID NO 30
<211> LENGTH: 12
<212> TYPE: PRT
<213> ORGANISM: Homo sapiens

<400> SEQUENCE: 30

Val Val Phe Gly Gly Gly Thr Lys Leu Thr Val Leu
1               5                   10

<210> SEQ ID NO 31
<211> LENGTH: 96
<212> TYPE: PRT
<213> ORGANISM: Homo sapiens

<400> SEQUENCE: 31

Ser Ser Glu Leu Thr Gln Asp Pro Ala Val Ser Val Ala Leu Gly Gln
1               5                   10                  15

Thr Val Arg Ile Thr Cys Gln Gly Asp Ser Leu Arg Ser Tyr Tyr Ala
                20                  25                  30

Ser Trp Tyr Gln Gln Lys Pro Gly Gln Ala Pro Val Leu Val Ile Tyr
            35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Arg Asp Ser Ser Gly Asn His
                85                  90                  95

<210> SEQ ID NO 32
<211> LENGTH: 17
<212> TYPE: PRT
<213> ORGANISM: Artificial sequence
<220> FEATURE:
<223> OTHER INFORMATION: Synthetic sequence: myc tag

<400> SEQUENCE: 32

Ala Ala Ala Glu Gln Lys Leu Ile Ser Glu Glu Asp Leu Asn Gly Ala
1               5                   10                  15

Ala

<210> SEQ ID NO 33
<211> LENGTH: 14
<212> TYPE: PRT
<213> ORGANISM: Artificial sequence
<220> FEATURE:
<223> OTHER INFORMATION: Synthetic sequence: Linker

<400> SEQUENCE: 33

```
Gly Gly Gly Gly Ser Gly Gly Gly Ser Gly Gly Gly
1               5                   10
```

<210> SEQ ID NO 34
<211> LENGTH: 119
<212> TYPE: PRT
<213> ORGANISM: Artificial sequence
<220> FEATURE:
<223> OTHER INFORMATION: Synthetic sequence: VH domain
<220> FEATURE:
<221> NAME/KEY: VARIANT
<222> LOCATION: (52)..(52)
<223> OTHER INFORMATION: Xaa is Asp or Lys
<220> FEATURE:
<221> NAME/KEY: VARIANT
<222> LOCATION: (99)..(102)
<223> OTHER INFORMATION: Xaa is an amino acid
<220> FEATURE:
<221> NAME/KEY: VARIANT
<222> LOCATION: (103)..(105)
<223> OTHER INFORMATION: Xaa is an amino acid or is not present

<400> SEQUENCE: 34

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45

Ser Ala Ile Xaa Gly Ser Gly Gly Ser Thr Tyr Tyr Ala Asp Ser Val
    50                  55                  60

Lys Gly Arg Phe Thr Ile Ser Arg Asp Asn Ser Lys Asn Thr Leu Tyr
65                  70                  75                  80

Leu Gln Met Asn Ser Leu Arg Ala Glu Asp Thr Ala Val Tyr Tyr Cys
                85                  90                  95

Ala Lys Xaa Xaa Xaa Xaa Xaa Xaa Phe Asp Tyr Trp Gly Gln Gly
            100                 105                 110

Thr Leu Val Thr Val Ser Ser
        115
```

<210> SEQ ID NO 35
<211> LENGTH: 119
<212> TYPE: PRT
<213> ORGANISM: Artificial sequence
<220> FEATURE:
<223> OTHER INFORMATION: Synthetic sequence: VH domain
<220> FEATURE:
<221> NAME/KEY: VARIANT
<222> LOCATION: (52)..(52)
<223> OTHER INFORMATION: Xaa is Asn or Tyr
<220> FEATURE:
<221> NAME/KEY: VARIANT
<222> LOCATION: (99)..(102)
<223> OTHER INFORMATION: Xaa is an amino acid
<220> FEATURE:
<221> NAME/KEY: VARIANT
<222> LOCATION: (103)..(105)
<223> OTHER INFORMATION: Xaa is an amino acid or is not present

<400> SEQUENCE: 35

```
Glu Val Gln Leu Leu Glu Ser Gly Gly Gly Leu Val Gln Pro Gly Gly
1               5                   10                  15

Ser Leu Arg Leu Ser Cys Ala Ala Ser Gly Phe Thr Phe Ser Ser Tyr
            20                  25                  30

Ala Met Ser Trp Val Arg Gln Ala Pro Gly Lys Gly Leu Glu Trp Val
        35                  40                  45
```

```
Ser Ala Ile Xaa Gly Ser Gly Gly Ser Thr Tyr Tyr Ala Asp Ser Val
        50                  55                  60

Lys Gly Arg Phe Thr Ile Ser Arg Asp Asn Ser Lys Asn Thr Leu Tyr
 65                  70                  75                  80

Leu Gln Met Asn Ser Leu Arg Ala Glu Asp Thr Ala Val Tyr Tyr Cys
                85                  90                  95

Ala Lys Xaa Xaa Xaa Xaa Xaa Xaa Phe Asp Tyr Trp Gly Gln Gly
            100                 105                 110

Thr Leu Val Thr Val Ser Ser
            115

<210> SEQ ID NO 36
<211> LENGTH: 108
<212> TYPE: PRT
<213> ORGANISM: Artificial sequence
<220> FEATURE:
<223> OTHER INFORMATION: Synthetic sequence: DPK22 VL domain
<220> FEATURE:
<221> NAME/KEY: VARIANT
<222> LOCATION: (92)..(97)
<223> OTHER INFORMATION: Xaa92, Xaa93, Xaa94, Xaa95 and Xaa97 are amino
      acid residues, and at least one of Xaa93 and Xaa94 is Gly

<400> SEQUENCE: 36

Glu Ile Val Leu Thr Gln Ser Pro Gly Thr Leu Ser Leu Ser Pro Gly
 1               5                  10                  15

Glu Arg Ala Thr Leu Ser Cys Arg Ala Ser Gln Ser Val Ser Ser Ser
                20                  25                  30

Tyr Leu Ala Trp Tyr Gln Gln Lys Pro Gly Gln Ala Pro Arg Leu Leu
            35                  40                  45

Ile Tyr Gly Ala Ser Ser Arg Ala Thr Gly Ile Pro Asp Arg Phe Ser
 50                  55                  60

Gly Ser Gly Ser Gly Thr Asp Phe Thr Leu Thr Ile Ser Arg Leu Glu
 65                  70                  75                  80

Pro Glu Asp Phe Ala Val Tyr Tyr Cys Gln Gln Xaa Xaa Xaa Xaa Pro
                85                  90                  95

Xaa Thr Phe Gly Gln Gly Thr Lys Val Glu Ile Lys
            100                 105

<210> SEQ ID NO 37
<211> LENGTH: 108
<212> TYPE: PRT
<213> ORGANISM: Artificial sequence
<220> FEATURE:
<223> OTHER INFORMATION: Synthetic sequence: DPL16 VL domain
<220> FEATURE:
<221> NAME/KEY: VARIANT
<222> LOCATION: (90)..(90)
<223> OTHER INFORMATION: Xaa is Ser or Arg
<220> FEATURE:
<221> NAME/KEY: VARIANT
<222> LOCATION: (91..93, 95, 96)
<223> OTHER INFORMATION: Xaa91, Xaa92, Xaa93, Xaa95, and Xaa96 are amino
      acid residues, at least one of which is Pro
<220> FEATURE:
<221> NAME/KEY: VARIANT
<222> LOCATION: (94)..(94)
<223> OTHER INFORMATION: Xaa is an amino acid residue

<400> SEQUENCE: 37

Ser Ser Glu Leu Thr Gln Asp Pro Ala Val Ser Val Ala Leu Gly Gln
 1               5                  10                  15

Thr Val Arg Ile Thr Cys Gln Gly Asp Ser Leu Arg Ser Tyr Tyr Ala
                20                  25                  30
```

-continued

```
Ser Trp Tyr Gln Gln Lys Pro Gly Gln Ala Pro Val Leu Val Ile Tyr
        35                  40                  45

Gly Lys Asn Asn Arg Pro Ser Gly Ile Pro Asp Arg Phe Ser Gly Ser
    50                  55                  60

Ser Ser Gly Asn Thr Ala Ser Leu Thr Ile Thr Gly Ala Gln Ala Glu
65                  70                  75                  80

Asp Glu Ala Asp Tyr Tyr Cys Asn Ser Xaa Xaa Xaa Xaa Xaa Xaa Xaa
                85                  90                  95

Val Val Phe Gly Gly Gly Thr Lys Leu Thr Val Leu
            100                 105

<210> SEQ ID NO 38
<211> LENGTH: 5
<212> TYPE: PRT
<213> ORGANISM: Artificial sequence
<220> FEATURE:
<223> OTHER INFORMATION: Synthetic sequence: VH domain

<400> SEQUENCE: 38

Glu Val Gln Leu Leu
1               5

<210> SEQ ID NO 39
<211> LENGTH: 7
<212> TYPE: PRT
<213> ORGANISM: Artificial sequence
<220> FEATURE:
<223> OTHER INFORMATION: Synthetic sequence: VH domain

<400> SEQUENCE: 39

Ala Ile Asp Gly Ser Ser Gly
1               5

<210> SEQ ID NO 40
<211> LENGTH: 22
<212> TYPE: PRT
<213> ORGANISM: Artificial sequence
<220> FEATURE:
<223> OTHER INFORMATION: Synthetic sequence: VH domain
<220> FEATURE:
<221> NAME/KEY: VARIANT
<222> LOCATION: (5)..(8)
<223> OTHER INFORMATION: Variable mutations may be present at any of the
      residue positions marked "Xaa"

<400> SEQUENCE: 40

Tyr Cys Ala Lys Xaa Xaa Xaa Xaa Phe Asp Tyr Trp Gly Gln Gly Thr
1               5                   10                  15

Leu Val Thr Val Ser Ser
            20

<210> SEQ ID NO 41
<211> LENGTH: 23
<212> TYPE: PRT
<213> ORGANISM: Artificial sequence
<220> FEATURE:
<223> OTHER INFORMATION: Synthetic sequence: VH domain
<220> FEATURE:
<221> NAME/KEY: VARIANT
<222> LOCATION: (5)..(9)
<223> OTHER INFORMATION: Variable mutations may be present at any of the
      residue positions marked "Xaa"

<400> SEQUENCE: 41

Tyr Cys Ala Lys Xaa Xaa Xaa Xaa Xaa Phe Asp Tyr Trp Gly Gln Gly
1               5                   10                  15
```

Thr Leu Val Thr Val Ser Ser
            20

<210> SEQ ID NO 42
<211> LENGTH: 24
<212> TYPE: PRT
<213> ORGANISM: Artificial sequence
<220> FEATURE:
<223> OTHER INFORMATION: Synthetic sequence: VH domain
<220> FEATURE:
<221> NAME/KEY: VARIANT
<222> LOCATION: (5)..(10)
<223> OTHER INFORMATION: Variable mutations may be present at any of the
      residue positions marked "Xaa"

<400> SEQUENCE: 42

Tyr Cys Ala Lys Xaa Xaa Xaa Xaa Xaa Xaa Phe Asp Tyr Trp Gly Gln
1               5                   10                  15

Gly Thr Leu Val Thr Val Ser Ser
            20

<210> SEQ ID NO 43
<211> LENGTH: 25
<212> TYPE: PRT
<213> ORGANISM: Artificial sequence
<220> FEATURE:
<223> OTHER INFORMATION: Synthetic sequence: VH domain
<220> FEATURE:
<221> NAME/KEY: VARIANT
<222> LOCATION: (5)..(11)
<223> OTHER INFORMATION: Variable mutations may be present at any of the
      residue positions marked "Xaa"

<400> SEQUENCE: 43

Tyr Cys Ala Lys Xaa Xaa Xaa Xaa Xaa Xaa Xaa Phe Asp Tyr Trp Gly
1               5                   10                  15

Gln Gly Thr Leu Val Thr Val Ser Ser
            20                  25

<210> SEQ ID NO 44
<211> LENGTH: 7
<212> TYPE: PRT
<213> ORGANISM: Artificial sequence
<220> FEATURE:
<223> OTHER INFORMATION: Synthetic sequence: VH domain

<400> SEQUENCE: 44

Ala Ile Lys Gly Ser Ser Gly
1               5

<210> SEQ ID NO 45
<211> LENGTH: 7
<212> TYPE: PRT
<213> ORGANISM: Artificial sequence
<220> FEATURE:
<223> OTHER INFORMATION: Synthetic sequence: VH domain

<400> SEQUENCE: 45

Ala Ile Asn Gly Ser Ser Gly
1               5

<210> SEQ ID NO 46
<211> LENGTH: 7
<212> TYPE: PRT
<213> ORGANISM: Artificial sequence
<220> FEATURE:
<223> OTHER INFORMATION: Synthetic sequence: VH domain

```
<400> SEQUENCE: 46

Ala Ile Tyr Gly Ser Ser Gly
1               5

<210> SEQ ID NO 47
<211> LENGTH: 7
<212> TYPE: PRT
<213> ORGANISM: Artificial sequence
<220> FEATURE:
<223> OTHER INFORMATION: Synthetic sequence: VL domain

<400> SEQUENCE: 47

Glu Ile Val Leu Thr Gln Ser
1               5

<210> SEQ ID NO 48
<211> LENGTH: 21
<212> TYPE: PRT
<213> ORGANISM: Artificial sequence
<220> FEATURE:
<223> OTHER INFORMATION: Synthetic sequence: VL domain
<220> FEATURE:
<221> NAME/KEY: VARIANT
<222> LOCATION: (5, 7, 8, 10)
<223> OTHER INFORMATION: Variable mutations may be present at any of the
      residue positions marked "Xaa"

<400> SEQUENCE: 48

Tyr Cys Gln Gln Xaa Gly Xaa Xaa Pro Xaa Thr Phe Gly Gln Gly Thr
1               5                   10                  15

Lys Val Glu Ile Lys
            20

<210> SEQ ID NO 49
<211> LENGTH: 21
<212> TYPE: PRT
<213> ORGANISM: Artificial sequence
<220> FEATURE:
<223> OTHER INFORMATION: Synthetic sequence: VL domain
<220> FEATURE:
<221> NAME/KEY: VARIANT
<222> LOCATION: (5, 6, 8, 10)
<223> OTHER INFORMATION: Variable mutations may be present at any of the
      residue positions marked "Xaa"

<400> SEQUENCE: 49

Tyr Cys Gln Gln Xaa Xaa Gly Xaa Pro Xaa Thr Phe Gly Gln Gly Thr
1               5                   10                  15

Lys Val Glu Ile Lys
            20

<210> SEQ ID NO 50
<211> LENGTH: 7
<212> TYPE: PRT
<213> ORGANISM: Artificial sequence
<220> FEATURE:
<223> OTHER INFORMATION: Synthetic sequence: VL domain

<400> SEQUENCE: 50

Ser Ser Glu Leu Thr Gln Asp
1               5

<210> SEQ ID NO 51
<211> LENGTH: 22
<212> TYPE: PRT
<213> ORGANISM: Artificial sequence
<220> FEATURE:
<223> OTHER INFORMATION: Synthetic sequence: VL domain
```

-continued

```
<220> FEATURE:
<221> NAME/KEY: VARIANT
<222> LOCATION: (6)..(10)
<223> OTHER INFORMATION: Variable mutations may be present at any of the
      residue positions marked "Xaa"

<400> SEQUENCE: 51

Cys Asn Ser Ser Pro Xaa Xaa Xaa Xaa Xaa Val Val Phe Gly Gly Gly
1               5                   10                  15

Thr Lys Leu Thr Val Leu
            20

<210> SEQ ID NO 52
<211> LENGTH: 22
<212> TYPE: PRT
<213> ORGANISM: Artificial sequence
<220> FEATURE:
<223> OTHER INFORMATION: Synthetic sequence: VL domain
<220> FEATURE:
<221> NAME/KEY: VARIANT
<222> LOCATION: (5)..(5)
<223> OTHER INFORMATION: Variable mutations may be present at any of the
      residue positions marked "Xaa"
<220> FEATURE:
<221> NAME/KEY: VARIANT
<222> LOCATION: (7)..(10)
<223> OTHER INFORMATION: Variable mutations may be present at any of the
      residue positions marked "Xaa"

<400> SEQUENCE: 52

Cys Asn Ser Ser Xaa Pro Xaa Xaa Xaa Xaa Val Val Phe Gly Gly Gly
1               5                   10                  15

Thr Lys Leu Thr Val Leu
            20

<210> SEQ ID NO 53
<211> LENGTH: 22
<212> TYPE: PRT
<213> ORGANISM: Artificial sequence
<220> FEATURE:
<223> OTHER INFORMATION: Synthetic sequence: VL domain
<220> FEATURE:
<221> NAME/KEY: VARIANT
<222> LOCATION: (5)..(6)
<223> OTHER INFORMATION: Variable mutations may be present at any of the
      residue positions marked "Xaa"
<220> FEATURE:
<221> NAME/KEY: VARIANT
<222> LOCATION: (8)..(10)
<223> OTHER INFORMATION: Variable mutations may be present at any of the
      residue positions marked "Xaa"

<400> SEQUENCE: 53

Cys Asn Ser Ser Xaa Xaa Pro Xaa Xaa Xaa Val Val Phe Gly Gly Gly
1               5                   10                  15

Thr Lys Leu Thr Val Leu
            20

<210> SEQ ID NO 54
<211> LENGTH: 22
<212> TYPE: PRT
<213> ORGANISM: Artificial sequence
<220> FEATURE:
<223> OTHER INFORMATION: Synthetic sequence: VL domain
<220> FEATURE:
<221> NAME/KEY: VARIANT
<222> LOCATION: (5)..(8)
<223> OTHER INFORMATION: Variable mutations may be present at any of the
      residue positions marked "Xaa"
<220> FEATURE:
<221> NAME/KEY: VARIANT
```

```
<222> LOCATION: (10)..(10)
<223> OTHER INFORMATION: Variable mutations may be present at any of the
      residue positions marked "Xaa"

<400> SEQUENCE: 54

Cys Asn Ser Ser Xaa Xaa Xaa Xaa Pro Xaa Val Val Phe Gly Gly Gly
1               5                   10                  15

Thr Lys Leu Thr Val Leu
            20

<210> SEQ ID NO 55
<211> LENGTH: 22
<212> TYPE: PRT
<213> ORGANISM: Artificial sequence
<220> FEATURE:
<223> OTHER INFORMATION: Synthetic sequence: VL domain
<220> FEATURE:
<221> NAME/KEY: VARIANT
<222> LOCATION: (5)..(9)
<223> OTHER INFORMATION: Variable mutations may be present at any of the
      residue positions marked "Xaa"

<400> SEQUENCE: 55

Cys Asn Ser Ser Xaa Xaa Xaa Xaa Xaa Pro Val Val Phe Gly Gly Gly
1               5                   10                  15

Thr Lys Leu Thr Val Leu
            20

<210> SEQ ID NO 56
<211> LENGTH: 6
<212> TYPE: PRT
<213> ORGANISM: Artificial sequence
<220> FEATURE:
<223> OTHER INFORMATION: Synthetic sequence: VH CDR3

<400> SEQUENCE: 56

Leu Val Pro Arg Lys Phe
1               5

<210> SEQ ID NO 57
<211> LENGTH: 6
<212> TYPE: PRT
<213> ORGANISM: Artificial sequence
<220> FEATURE:
<223> OTHER INFORMATION: Synthetic sequence: VH CDR3

<400> SEQUENCE: 57

Leu Ser Ala Arg Arg Gly
1               5

<210> SEQ ID NO 58
<211> LENGTH: 6
<212> TYPE: PRT
<213> ORGANISM: Artificial sequence
<220> FEATURE:
<223> OTHER INFORMATION: Synthetic sequence: VH CDR3

<400> SEQUENCE: 58

Leu Thr Pro Gly Arg Phe
1               5

<210> SEQ ID NO 59
<211> LENGTH: 6
<212> TYPE: PRT
<213> ORGANISM: Artificial sequence
<220> FEATURE:
<223> OTHER INFORMATION: Synthetic sequence: VH CDR3
```

-continued

```
<400> SEQUENCE: 59

Ser Arg Gly Leu Ala Ile
1               5

<210> SEQ ID NO 60
<211> LENGTH: 6
<212> TYPE: PRT
<213> ORGANISM: Artificial sequence
<220> FEATURE:
<223> OTHER INFORMATION: Synthetic sequence: VL(DPL16) CDR3

<400> SEQUENCE: 60

Gly Gly Pro Val Thr Gly
1               5

<210> SEQ ID NO 61
<211> LENGTH: 6
<212> TYPE: PRT
<213> ORGANISM: Artificial sequence
<220> FEATURE:
<223> OTHER INFORMATION: Synthetic sequence: VL(DPL16) CDR3

<400> SEQUENCE: 61

Arg Arg Gly Arg Tyr Pro
1               5

<210> SEQ ID NO 62
<211> LENGTH: 6
<212> TYPE: PRT
<213> ORGANISM: Artificial sequence
<220> FEATURE:
<223> OTHER INFORMATION: Synthetic sequence: VL(DPL16) CDR3

<400> SEQUENCE: 62

Asn Arg Pro Arg Asn Lys
1               5

<210> SEQ ID NO 63
<211> LENGTH: 6
<212> TYPE: PRT
<213> ORGANISM: Artificial sequence
<220> FEATURE:
<223> OTHER INFORMATION: Synthetic sequence: VL(DPL16) CDR3

<400> SEQUENCE: 63

Tyr Pro His Phe Pro Arg
1               5
```